(12) United States Patent
Einarsson

(10) Patent No.: US 12,114,892 B2
(45) Date of Patent: *Oct. 15, 2024

(54) TROCARS AND VERESS-TYPE NEEDLES WITH ILLUMINATED GUIDANCE AND SAFETY FEATURES

(71) Applicant: The Brigham and Womens Hospital, Inc., Boston, MA (US)

(72) Inventor: Jon I. Einarsson, Boston, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 67 days.

This patent is subject to a terminal disclaimer.

(21) Appl. No.: 17/711,262

(22) Filed: Apr. 1, 2022

(65) Prior Publication Data

US 2022/0240978 A1 Aug. 4, 2022

Related U.S. Application Data

(63) Continuation of application No. 17/501,232, filed on Oct. 14, 2021, now Pat. No. 11,382,662, which is a continuation-in-part of application No. 17/368,296, filed on Jul. 6, 2021, which is a continuation-in-part of application No. 16/780,938, filed on Feb. 4, 2020, (Continued)

(51) Int. Cl.
*A61B 1/00* (2006.01)
*A61B 17/34* (2006.01)
*A61B 90/30* (2016.01)

(52) U.S. Cl.
CPC ...... *A61B 17/3474* (2013.01); *A61B 17/3423* (2013.01); *A61B 17/3496* (2013.01); *A61B 90/30* (2016.02); *A61B 2017/3456* (2013.01)

(58) Field of Classification Search
CPC ............ A61B 17/3474; A61B 17/3423; A61B 17/3496; A61B 2017/3456; A61B 90/30
See application file for complete search history.

(56) References Cited

U.S. PATENT DOCUMENTS

| 4,254,762 A | 3/1981 | Yoon |
| 5,104,381 A * | 4/1992 | Gresl ................. A61B 1/00135 D24/146 |

(Continued)

FOREIGN PATENT DOCUMENTS

| GB | 2481727 A | 1/2012 |
| WO | 1995013751 A1 | 5/1995 |

(Continued)

OTHER PUBLICATIONS

Extended European Search Report dated Mar. 2, 2021 from related application No. EP 18840663.1.

(Continued)

*Primary Examiner* — Timothy J Neal
(74) *Attorney, Agent, or Firm* — DeWitt LLP; Brian R. Pollack, Esq.

(57) ABSTRACT

The present disclosure provides devices and methods for insufflating abdomens of subjects under direct visualization. Such devices and methods, in some implementations, include features for cleaning the devices, and certain implementations of the methods permit procedures wherein it is not necessary to use a typical obturator to place a cannula, resulting in safer procedures.

20 Claims, 26 Drawing Sheets

Related U.S. Application Data now Pat. No. 11,051,851, which is a continuation-in-part of application No. PCT/US2018/045380, filed on Aug. 6, 2018.

(60) Provisional application No. 63/139,298, filed on Jan. 19, 2021, provisional application No. 62/541,644, filed on Aug. 4, 2017.

(56) References Cited

U.S. PATENT DOCUMENTS

| | | |
|---|---|---|
| 5,169,397 A | 12/1992 | Sakashita et al. |
| 5,209,721 A | 5/1993 | Wilk |
| 5,271,380 A | 12/1993 | Riek et al. |
| 5,290,276 A | 3/1994 | Sewell, Jr. |
| 5,383,859 A | 1/1995 | Sewell, Jr. |
| 5,609,562 A | 3/1997 | Kaali |
| 5,697,888 A | 12/1997 | Kobayashi et al. |
| 7,708,713 B2 | 5/2010 | Albrecht et al. |
| 7,927,272 B2 | 4/2011 | Bayer et al. |
| 8,128,590 B2 | 3/2012 | Albrecht et al. |
| 8,267,952 B2 | 9/2012 | Kahle et al. |
| 8,517,977 B2 | 8/2013 | Taylor et al. |
| 8,838,206 B2 | 9/2014 | Mohajer |
| 11,382,662 B2 * | 7/2022 | Einarsson .......... A61B 1/00096 |
| 2005/0288622 A1 | 12/2005 | Albrecht et al. |
| 2006/0276692 A1 | 12/2006 | Kucklick |
| 2007/0282253 A1 | 12/2007 | Sasaki |
| 2008/0004634 A1 | 1/2008 | Farritor et al. |
| 2008/0243162 A1 | 10/2008 | Shibata et al. |
| 2009/0248036 A1 | 10/2009 | Hoffman |
| 2010/0168520 A1 | 7/2010 | Poll et al. |
| 2010/0191260 A1 | 7/2010 | Mohajer |
| 2010/0274081 A1 | 10/2010 | Okoniewski |
| 2011/0313255 A1 | 12/2011 | Stanley et al. |
| 2012/0197078 A1 | 8/2012 | Stanley |
| 2014/0275986 A1 | 9/2014 | Vertikov |
| 2015/0282695 A1 | 10/2015 | Tay et al. |
| 2017/0042573 A1 * | 2/2017 | Savvouras ......... A61B 1/00154 |
| 2017/0173275 A1 | 6/2017 | Anderson |
| 2020/0170672 A1 | 6/2020 | Einarsson |

FOREIGN PATENT DOCUMENTS

| | | |
|---|---|---|
| WO | 2012077117 A1 | 6/2012 |
| WO | 2017079662 A1 | 5/2017 |
| WO | 2019028458 A1 | 2/2019 |

OTHER PUBLICATIONS

Search Report dated Nov. 26, 2021 in related European Patent Application No. 18 840 663.1.
International Search Report and Written Opinion mailed Oct. 24, 2018 for corresponding International Patent Application PCT/US2018/045380.
Silay et al., "The All-Seeing Needle Instead of the Veress Needle in Pediatric Urologic Laparoscopy," J. Endourology, 27(11):1376-1380 (Nov. 2013).
International Search Report dated May 6, 2022 in related International Patent Application No. PCT/US2022/12652.
Written Opinion of the International Searching Authority dated May 6, 2022 in related International Patent Application No. PCT/US2022/12652.

* cited by examiner

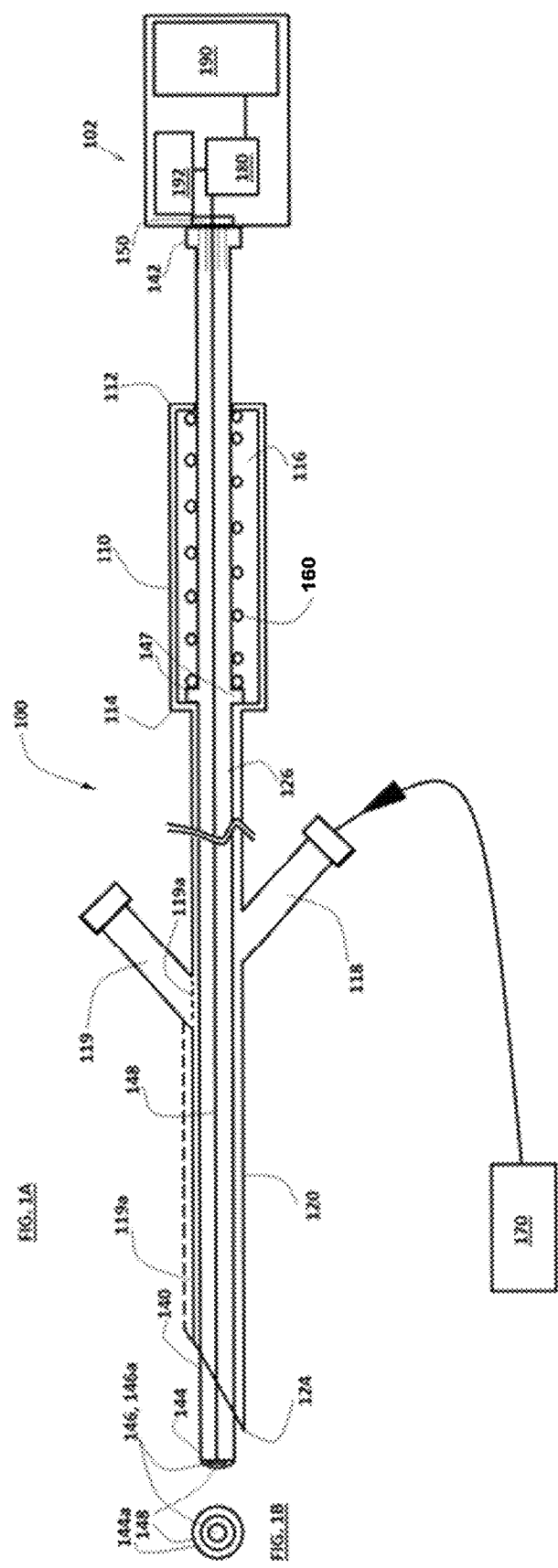

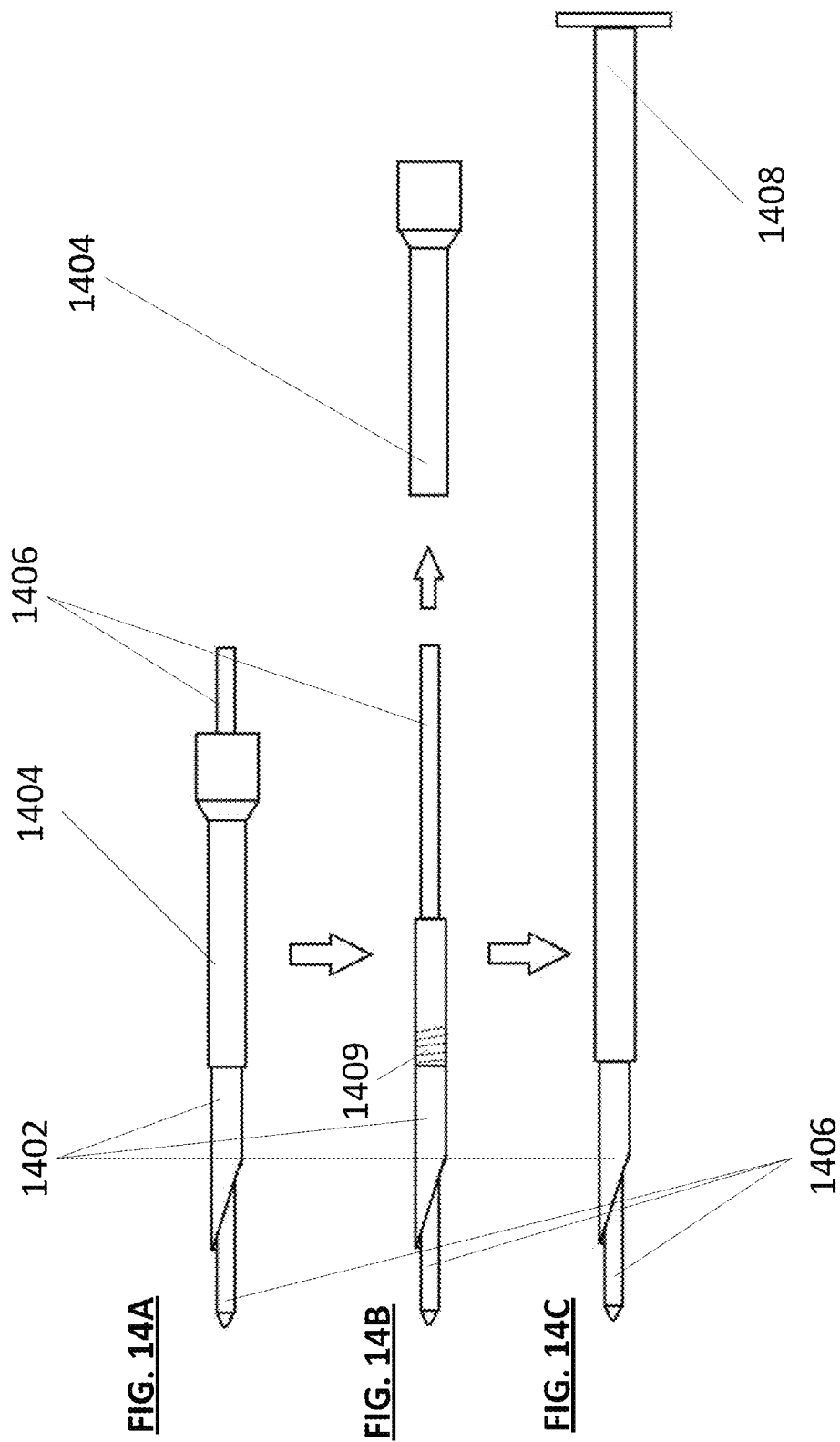

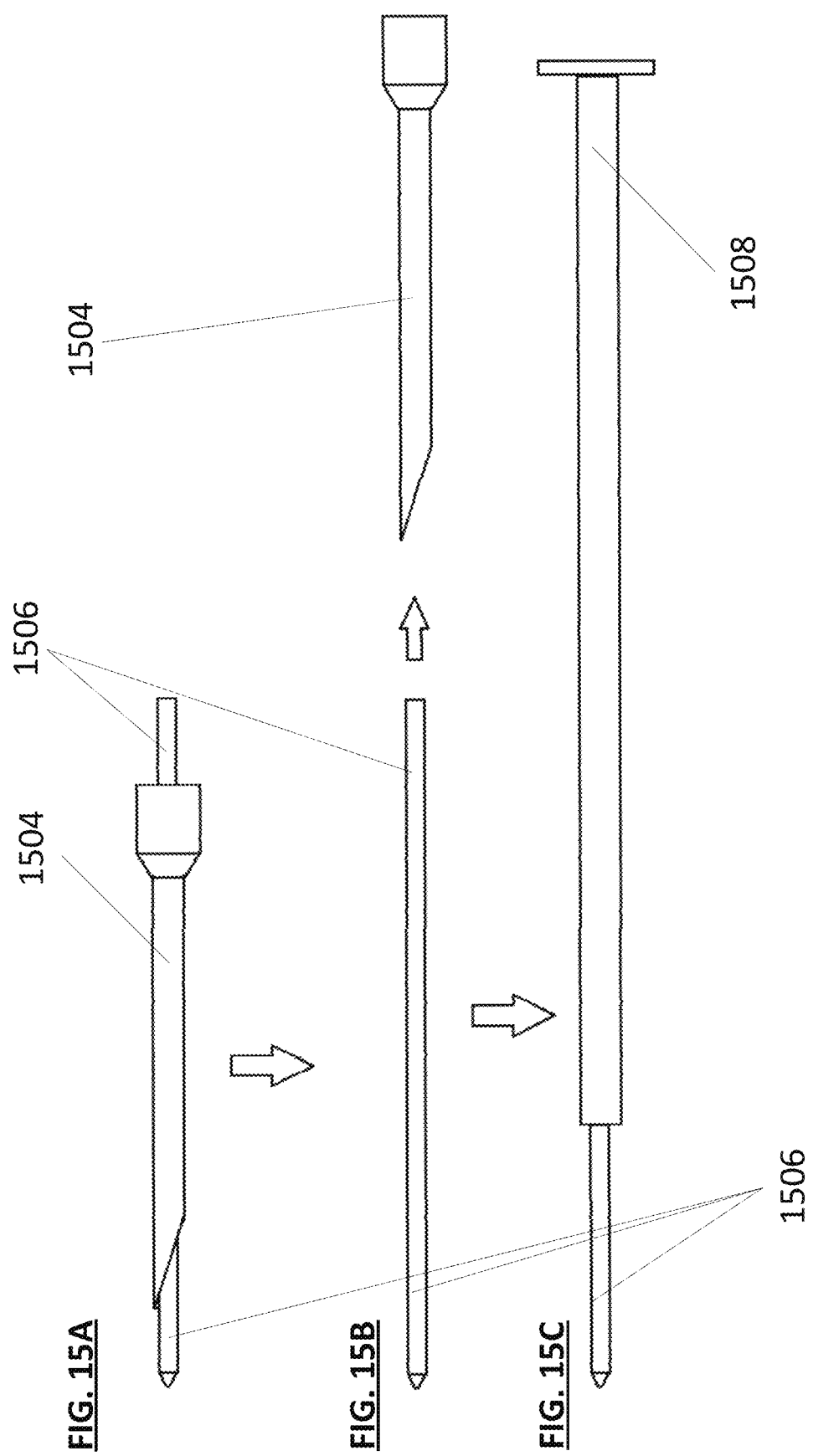

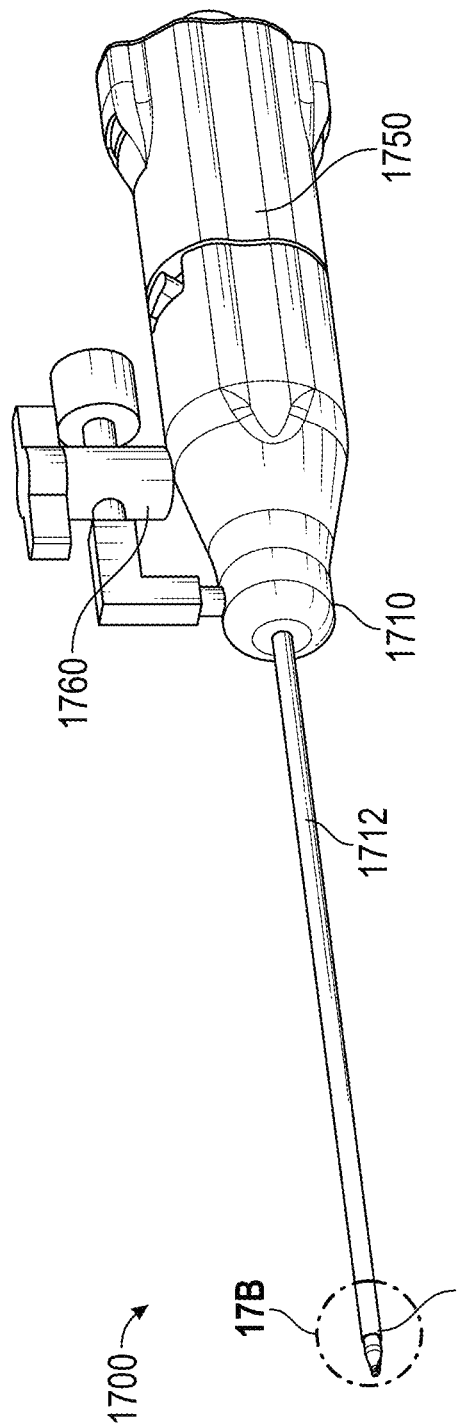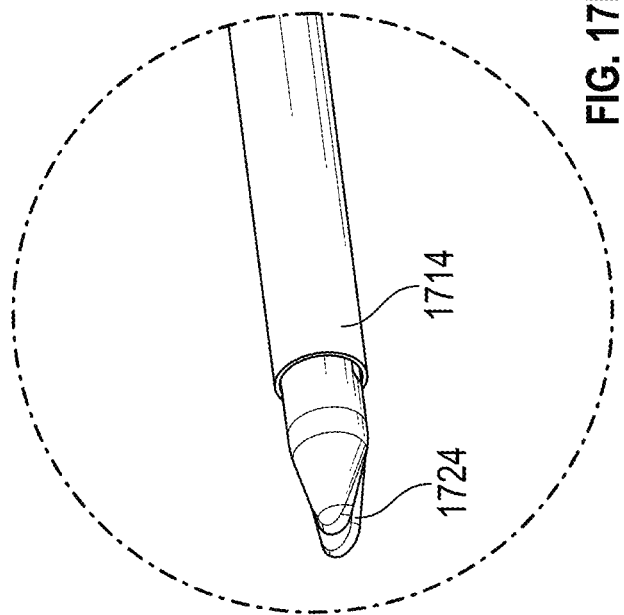
FIG. 17A
FIG. 17B

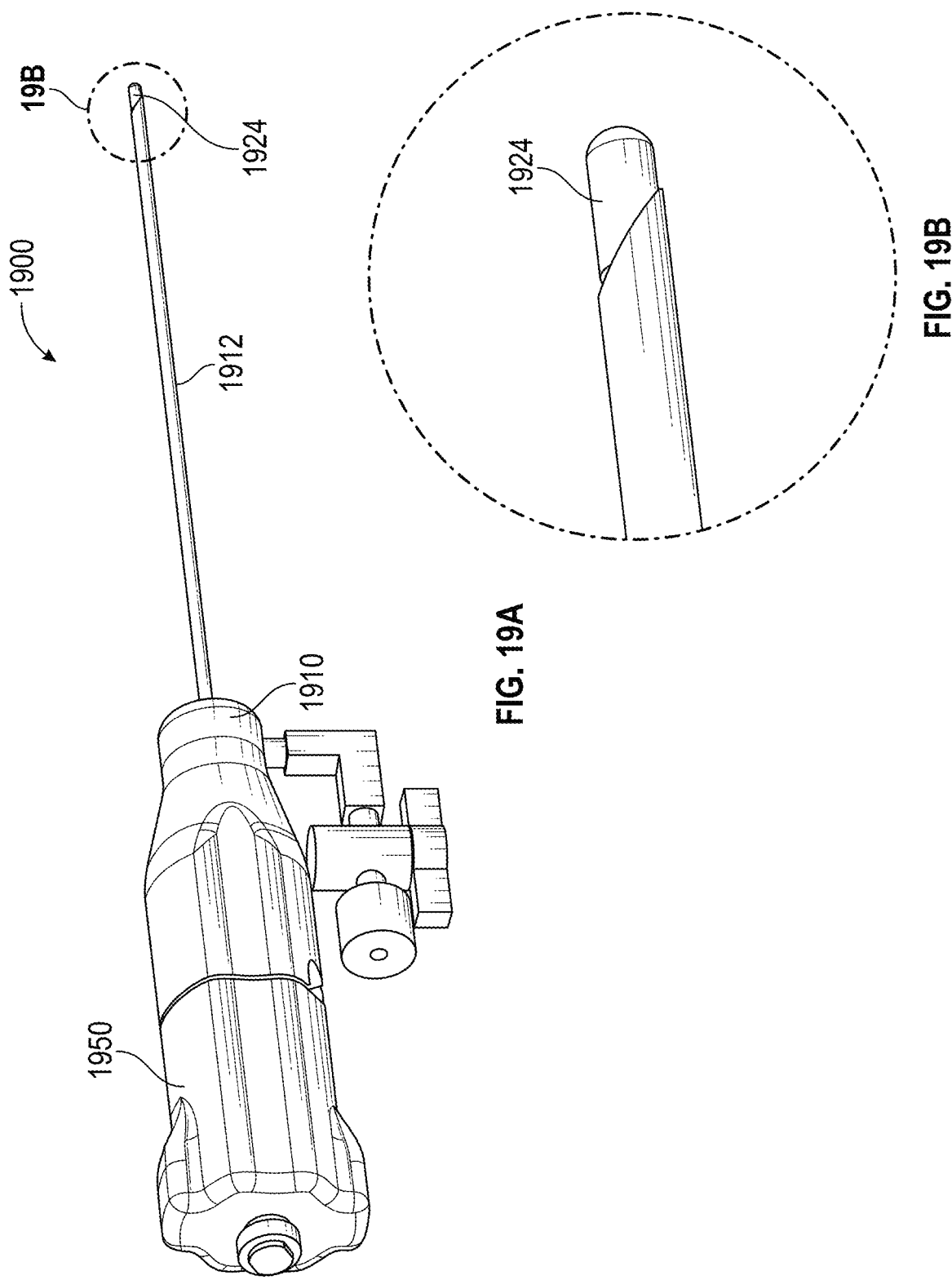

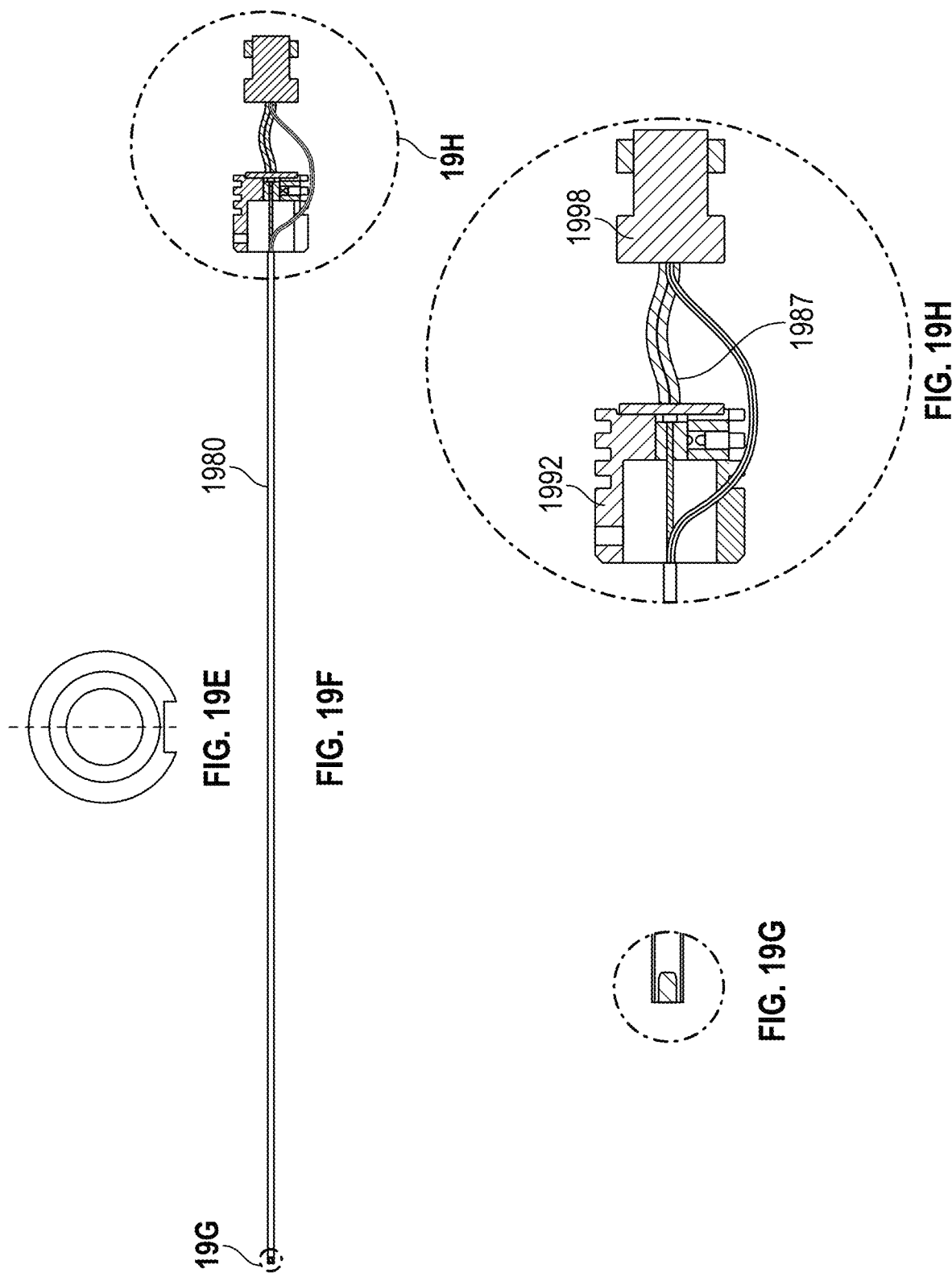

TROCARS AND VERESS-TYPE NEEDLES WITH ILLUMINATED GUIDANCE AND SAFETY FEATURES

CROSS-REFERENCE TO RELATED APPLICATION

This patent application is a continuation of and claims the benefit of priority to U.S. patent application Ser. No. 17/501,232, filed Oct. 14, 2021, which in turn is a continuation-in-part of and claims the benefit of priority to U.S. patent application Ser. No. 17/368,296, filed Jul. 6, 2021, which in turn is a continuation-in-part of and claims the benefit of priority to U.S. patent application Ser. No. 16/780,938, filed Feb. 4, 2020, now U.S. Pat. No. 11,051,851, which in turn is a continuation-in-part of and claims the benefit of priority to International Patent Application No. PCT/US2018/45380, filed Aug. 6, 2018, which in turn is related to and claims the benefit of priority to U.S. Provisional Patent Application No. 62/541,644, filed Aug. 4, 2017. The present patent application also claims the benefit of priority to U.S. Provisional Patent Application No. 63/139,298, filed Jan. 19, 2021. Each of the foregoing patent applications is hereby incorporated by reference in its entirety for any purpose whatsoever.

BACKGROUND

Field

This disclosure relates to instruments and methods of use therefore in the practice of laparoscopic surgery and more particularly to such devices that have utility in forming an incision and insufflating the underlying body cavity in a safer manner than prior art devices.

Description of Related Art

In the practice of minimally invasive laparoscopic surgery it is common to make a small incision through the skin and underlying tissue of the patient, or subject, adjacent the internal surgical site using a Veress needle. These needles include a tubular outer cannula with a sharpened distal end and an inner hollow cylindrical needle, or cannula, which terminates in a blunt end. A spring assembly urges the inner cannula forward so that the blunt end of the inner cannula extends beyond the cutting edge of the outer cannula. When the instrument is pressed against the skin of the patient the inner blunt cannula retracts thereby permitting the outer sharp cannula to contact the skin and advance into the tissue. As soon as a body cavity is entered, the inner blunt cannula springs forward, so that the accidental cutting of underlying organs by the sharpened outer cannula is avoided.

The Veress needle typically includes means for introducing pressurized gas, usually $CO_2$, into the proximal end of the needle so that the gas is passed on through the laparoscopic incision and inflates the body cavity to allow easy access to the surgical site. After formation of a first incision and insufflation of the body cavity, the Veress needle is typically removed and a trocar is placed through the same incision.

One problem associated with the use of such Veress needle assemblies is determining when the needle has progressed through the wall of the body cavity and its distal end has emerged within the cavity. Additionally, inadvertent injury to internal organs such as bowel and major blood vessels may occur during the insertion of a standard Veress needle. This happens because this initial entry is blind (i.e., the surgeon cannot see where the needle is going). The present disclosure provides solutions to these and other problems in the art, as set forth below.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

In accordance with one aspect, the present disclosure is directed to an apparatus that includes a handle having proximal end and distal end connected at the distal end to a hollow distally extending needle having a distal end for penetrating tissue and a proximal end, wherein the handle and hollow distally extending needle form a conduit for passing at least one of fluid or instruments therethrough. The apparatus further includes a visualization stylet having a proximal end and a distal end, said visualization stylet being slidably disposed within the conduit, wherein a distal end region of the visualization stylet includes an electronic photodetector chip mounted thereon having a distally facing surface configured to detect incoming light traveling along a proximal direction. The visualization stylet can further include a light source configured to project light beyond the electronic photodetector chip in a distal direction to provide direct illumination, wherein light originating from the light source is reflected back to the electronic photodetector chip when the apparatus is traveling through tissue. The apparatus can further include a spring housed within the handle for biasing the visualization stylet to extend past the sharp distal end of the hollow distally extending needle absent resistance by tissue against the visualization stylet.

In further implementations, the visualization stylet can include a lens element disposed on a distal tip thereof over the electronic photodetector chip. In some embodiments, the lens element can directly contact the electronic photodetector chip. In some implementations, the lens element can be axially spaced with respect to the electronic photodetector chip. If desired, the lens element can be controllably, adjustably axially spaced with respect to the electronic photodetector chip to permit a user to focus incoming light passing through the lens onto the electronic photodetector chip. For example, axial spacing of the lens element from the electronic photodetector chip along a central longitudinal axis of the apparatus can be adjusted by sliding the lens element with respect to the electronic photodetector chip.

If desired, axial spacing of the lens element from the electronic photodetector chip along a central longitudinal axis of the apparatus can be adjusted by rotating the lens element with respect to the electronic photodetector chip. In some embodiments, the lens element can include a convex lens, a plano-convex lens, or other lens. The lens element can be, for example, conically shaped, pyramid-shaped, or dome shaped, among others. In some implementations, the lens element can include a central lens configured to focus incoming light on the electronic photodetector chip surrounded by a plurality of secondary lenses configured and arranged to disperse light transmitted distally from the lens element originating from the light source.

In some embodiments, the light source can includes a bundle of fiber optic elements coupled to a source of light. If desired, the light source can include at least one micro-LED element surrounding the electronic photodetector chip. The at least one micro-LED element can include an optic disposed thereon that focuses and directs light from the at least one micro-LED element onto at least one of the secondary lenses. If desired, the lens element can include a central lens configured to focus incoming light on the electronic photodetector chip surrounded by an annular region of the lens, wherein the central lens is radially separated from the annular region of the lens by at least one fluid flow channel configured and arranged to direct a jet of cleaning fluid over at least a portion of the central lens. In some implementations, the central lens and the annular region of the lens can be integrally molded. If desired, the central lens and the annular region of the lens can be formed from at least two discrete components.

In some implementations, the apparatus can further include at least one fluid flow channel configured and arranged to direct a jet of cleaning fluid over at least a portion of a central lens disposed at the distal end of the visualization stylet. The at least one fluid flow channel can be defined by at least one tubular member slidably disposed along the visualization stylet, the tubular member(s) defining a plurality of spray openings in a side wall thereof. If desired, the tubular member(s) can be formed from a shape memory material. A distal region of the tubular member(s) can be advanced distally out from the visualization stylet, and takes on a heat set curvature that causes the tubular member to bend toward the lens element.

In some embodiments, if correspondingly equipped, the axial spacing of the lens element from the electronic photodetector chip can be adjusted by actuating an actuator near a proximal end of the visualization stylet. If desired, any of the lens elements disclosed herein can include at least one vent hole therein, for example, for passage of insufflation gas, and/or to facilitate the focusing of the lens element by permitting axial repositioning of the lens with respect to the rest of the visualization stylet.

In some embodiments, the at least one fluid flow channel can be defined by at least one tubular member attached to an inner wall of the conduit of the hollow needle. The tubular member can define a plurality of spray openings in a side wall thereof configured and arranged to clean the lens by directing a transverse flow of fluid across the lens. The visualization stylet can also define at least one elongate insufflation conduit therein configured to pass insufflation gas therethrough to a distal end region of the apparatus. Insufflation gas can exit through at least one opening defined through a sidewall of the visualization stylet near a distal tip of the visualization stylet. The visualization stylet can be formed at least in part from a light transmitting material. The light source can include at least one LED disposed in the proximal end of the handle, for example.

In some implementations, the apparatus can further include a gas introduction port for receiving insufflation gas from a gas source. The visualization stylet can be configured to be withdrawn proximally to establish a flow path for insufflation gas to pass through the apparatus. The visualization stylet can further include a conductor for directing signals received from the electronic photodetector chip to a processor. The processor can be attached to the visualization stylet. If desired, the apparatus can further include a display screen for displaying images captured by the electronic photodetector chip. If desired, the apparatus can further include a battery for powering the electronic photodetector chip, processor and display screen.

The disclosure further provides a variety of methods for treating subject, such as a patient. For example, a first embodiment of a method is provided of using devices such as those described herein. Some of the methods can include creating a small superficial incision in skin of an abdomen of a subject, advancing a distal end of a hollow distally extending needle including a visualization stylet disposed therein through successive layers of an abdominal wall of the subject while viewing tissue being advanced through by way of the visualization stylet in real time, the visualization stylet being configured to view in a distal direction, and stopping advancing the distal end of the hollow distally extending needle upon observing the visualization stylet extending distally with respect to the hollow distally extending needle indicating that an abdominal cavity of the subject has been reached.

In some implementations, the method can further include commencing insufflation through the hollow distally extending needle after stopping advancing the distal end of the hollow distally extending needle. Commencing insufflation through the hollow distally extending needle can further include removing the visualization stylet through the proximal end of the hollow distally extending needle and injecting gas through the hollow distally extending needle. If desired, the method can further include comprising directing signals from the electronic photodetector chip to a processor. The method can further include directing signals from the processor to a display screen.

In some embodiments of the method, the hollow distally extending needle can act as a sheath that at least partially covers the visualization stylet along its length. The handle can include a cannula that is removably attached to the hollow distally extending needle. The method can further include, after insufflation, removing the cannula from the hollow distally extending needle and withdrawing the cannula proximally over the visualization stylet. Removing the cannula can include disconnecting a threaded connection joining the hollow distally extending needle and the cannula. If desired, the method can further include attaching a proximal extension to at least one of the hollow distally extending needle and the visualization stylet to form an assembly, and performing a laparoscopic procedure using the assembly as an endoscope. If desired, the method can further include separating the hollow distally extending needle and handle from the visualization stylet and removing one of the visualization stylet and hollow distally extending needle and handle from the subject. Once the visualization stylet is removed, the method can include leaving the hollow distally extending needle in place to function as a cannula for performing a further procedure.

The method, can further include, in some embodiments, removing a lens cap from the visualization stylet, and reintroducing the visualization stylet into the handle and the hollow distally extending needle without the lens cap. The lens cap can be removed, for example, by articulating the lens cap away from the distal end of the visualization stylet on a hinge.

Disclosed methods can also include, for example, directing a cleaning fluid including at least one of a liquid or gas at least partly in a transverse direction across the distal end of the visualization stylet while inside the subject to enhance visualization. Directing a cleaning fluid can include distally extending a cleaning wand that is configured and adapted to direct cleaning fluid toward the distal end of the visualization stylet. Directing the cleaning fluid can include directing the cleaning fluid through the visualization stylet and out through at least one opening at the distal end region of the visualization stylet. Directing the cleaning fluid can include directing the cleaning fluid through a lens located at the distal end of the visualization stylet. The cleaning fluid can be directed at least partially along a radially inward path across a central region of the lens. Directing the cleaning fluid can include directing the cleaning fluid through the hollow distally extending needle. If desired, directing the cleaning fluid can include directing the cleaning fluid through at least one tubular passage disposed between the visualization stylet and an inner bore of the hollow distally extending needle, wherein the at least one tubular passage is attached to the inner bore of the hollow distally extending needle.

In further accordance with the disclosure, the method can include removing the hollow distally extending needle and handle, leaving the visualization stylet in place. If desired, the method can further include adding a proximal extension to the visualization stylet to form an assembly, and using the assembly as an endoscope. The method can further include disposing a cannula having a bore diameter at least twice the diameter of the visualization stylet over the visualization stylet, causing the tissue to dilate radially outwardly. If desired, the visualization stylet can have a diameter of 1 to 2 mm, for example, and the cannula can have a 5 mm bore. If desired, the visualization stylet can have a diameter of 1 to 2 mm, and the cannula can have a 10 mm bore.

If desired, the method can further include withdrawing the visualization stylet, leaving the cannula in place. The method can further include introducing a further instrument through the cannula. The further instrument can be an endoscope configured to match a size of a bore of the cannula.

In further accordance with the disclosure, implementations of a surgical instrument are provided. In some implementations, the surgical instrument includes a distal outer assembly including a distal housing having a fluid input port and a hollow distally extending needle extending distally therefrom. The hollow distally extending needle has a distal end and a proximal end, wherein the distal outer assembly forms a passageway to pass at least one of fluid and instruments therethrough. The surgical instrument further includes a visualization stylet assembly at least partially disposed within the passageway of the distal outer assembly. The visualization stylet assembly is removably coupled to the distal outer assembly. The visualization stylet includes an elongate body having a proximal end and a distal end, an electronic photodetector chip mounted proximate the distal end of the elongate body, the electronic photodetector chip having a distally facing surface to detect incoming light traveling along a proximal direction, a light source at least partially integrated into the elongate body to project light beyond the electronic photodetector chip in a distal direction to provide direct illumination to guide passage of the insufflation needle assembly, and a sleeve slidably disposed about at least a distal tip region of the removable visualization stylet assembly. The sleeve can include a lens element disposed at a distal end thereof to direct light through the lens element toward the electronic photodetector chip. At least a portion of the sleeve can extend proximally through the hollow distally extending needle. The sleeve can terminate in a proximal handle portion of the sleeve to facilitate relative movement of the sleeve to the elongate body. The distal outer assembly and the removable visualization stylet assembly can be removably coupled together with the sleeve to permit the outer assembly, removable visualization stylet, and sleeve to be advanced through tissue as a single structural unit.

In some implementations, the visualization stylet assembly can be configured to be removed from the distal outer assembly with the sleeve, and the sleeve can be removed from around the removable visualization stylet assembly to expose the electronic photodetector chip and to permit the removable visualization stylet assembly to be reintroduced into the conduit of the outer assembly without the sleeve thereon.

In some implementations, the surgical instrument can be an insufflation needle assembly, or can be a trocar assembly. As an insufflation needle assembly, the removable visualization stylet assembly can include a proximal housing portion defining a bore therein that includes a compression spring disposed therein. The elongate body of the visualization stylet assembly can be biased in a distal direction with respect to the proximal housing portion by the compression spring to cause the sleeve and elongate body to extend beyond the distal end of the hollow distally extending needle. In some embodiments, the visualization stylet assembly can further include a connector body disposed concentrically about a proximal region of the elongate body. The connector body can include a distally facing connector to removably couple to the handle portion of the sleeve.

The visualization stylet assembly can further include a connector body disposed concentrically about a proximal region of the elongate body, and the connector body can include a distally facing connector to removably couple to the handle portion of the sleeve, the connector body being received at least partially within the proximal housing of the surgical instrument. If desired, the handle of the sleeve can include a female locking member that is received by a male locking member of the connector body (or vice-versa) to permit the sleeve to be selectively decoupled from the visualization stylet assembly to expose the electronic photodetector chip.

In some implementations, the proximal housing can define a distally extending boss to be sealingly received by the distal outer assembly. The distally extending boss can be surrounded by a fluid tight seal to interface with an inwardly facing surface of the distal outer assembly. The distal outer assembly can further include a guide tube, of a funnel shape, for example, disposed within the passageway of the distal outer body to guide the visualization stylet assembly into the hollow distally extending needle.

In some implementations, the visualization stylet assembly can further include a heat sink at least partially disposed within the proximal housing to dissipate heat generated by the surgical instrument. If desired, the proximal housing can define a proximal cavity in which the elongate body of the visualization terminates at the proximal end of the elongate body. At least one cable can extend from the proximal end of the elongate body through the proximal cavity, through the heat sink, and to a connector located within a proximal cap of the proximal housing. If desired, the heat sink can include a proximal end, a distal end and define a bore at least partially therethrough. A LED chip can be mounted at least partially within the bore of the heat sink. The LED chip can include a distally facing LED to direct light into the visualization stylet to provide forward illumination.

In further accordance with the disclosure, implementations of an insufflation needle assembly is provided that includes a distal assembly including a hollow distally extending needle having a sharpened distal end, a proximal end, and defining a needle bore therethrough. The hollow distally extending needle can be coupled at the proximal end thereof to a distal housing. The distal housing can define a proximal opening therein leading to a cavity. The cavity can be in fluid communication with the needle bore. The insufflation needle assembly can further include a proximal assembly that includes a proximal housing, a compression spring disposed in a bore of the proximal housing, and a visualization stylet. The visualization stylet can include (i) an elongate body defining a proximal end and a distal end, (ii) an electronic photodetector chip mounted proximate the distal end of the elongate body, the electronic photodetector chip having a distally facing surface to detect incoming light traveling along a proximal direction, (iii) a light source at least partially integrated into the elongate body to project light beyond the electronic photodetector chip in a distal direction to provide direct illumination to guide passage of the insufflation needle assembly, and (iv) a boss in contact with a distal end of the compression spring to urge the visualization stylet in a distal direction, for example. The proximal assembly can be configured to be received by the distal assembly and the proximal assembly can be configured to be removably coupled to the distal assembly. The visualization stylet can be biased to extend beyond the distal end of the hollow distally extending needle.

In some implementations, the proximal housing can form a handle of the device. The handle can be defined by a distal handle segment that is received by the distal housing. The distal handle segment can include a peripheral seal to interface with an inwardly facing surface of the distal housing. The handle can further include a proximal handle segment sealingly received by the distal handle segment, wherein the proximal handle segment and distal handle segment cooperate to define a spring bore to receive the compression spring. The boss of the visualization stylet can be disposed within the spring bore at a location distal relative to the compression spring. The compression spring surrounds a length of the elongate body of the visualization stylet located proximal to the boss. If desired, the spring can be removed from the handle by separating the proximal handle segment from the distal handle segment and withdrawing the elongate member from the distal handle segment while the elongate body is coupled to the proximal handle segment.

In some implementations, the proximal handle segment can define a proximally facing bore. The elongate body of the visualization stylet can terminate at a proximal end thereof within the proximally facing bore and be attached to a bushing that is sealingly received within the proximally facing bore of the proximal handle segment.

In some implementations, the proximal handle segment can be coupled at a proximal end thereof to a strain relief assembly. The strain relief assembly can define a region of varying stiffness. The strain relief assembly can terminate proximally in a plurality of connectors. The connectors can be coupled to conductors that traverse the elongate body of the visualization stylet. In some implementations, the conductors can traverse distally from the connectors, through the strain relief assembly, through the proximal cavity of the proximal handle segment, and into the elongate body of the visualization stylet. If desired, the strain relief can include a distally extending boss that is received within a proximal end of the proximally facing bore of the proximal handle segment. In some implementations, the distal assembly can be coupled to the proximal assembly in at least two discrete axially distinct positions.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

BRIEF DESCRIPTION OF THE DRAWINGS

Other objects, advantages and applications of the present disclosure will be made apparent by the following detailed description. The description makes reference to the accompany drawings in which:

FIGS. 1A-FIG. 1B present various views of a first embodiment in accordance with the present disclosure.

FIGS. 14A-FIG. 14C present views of steps of a method in accordance with the present disclosure.

FIGS. 15A-FIG. 15C present views of steps of still a further method in accordance with the present disclosure.

FIG. 17A is an isometric view of an optical trocar assembly in accordance with the present disclosure.

FIG. 17B is a close up view of a portion of the device depicted in FIG. 17A.

FIGS. 19A-19B illustrate full and partial isometric views of a spring loaded insufflation needle assembly in accordance with the present disclosure.

FIGS. 19E-19H are views of an optical probe portion of the device of FIG. 19A.

FIGS. 20E-20I show still further aspects of the embodiment of FIG. 20A.

DETAILED DESCRIPTION OF PREFERRED EMBODIMENTS

Figure 2A:
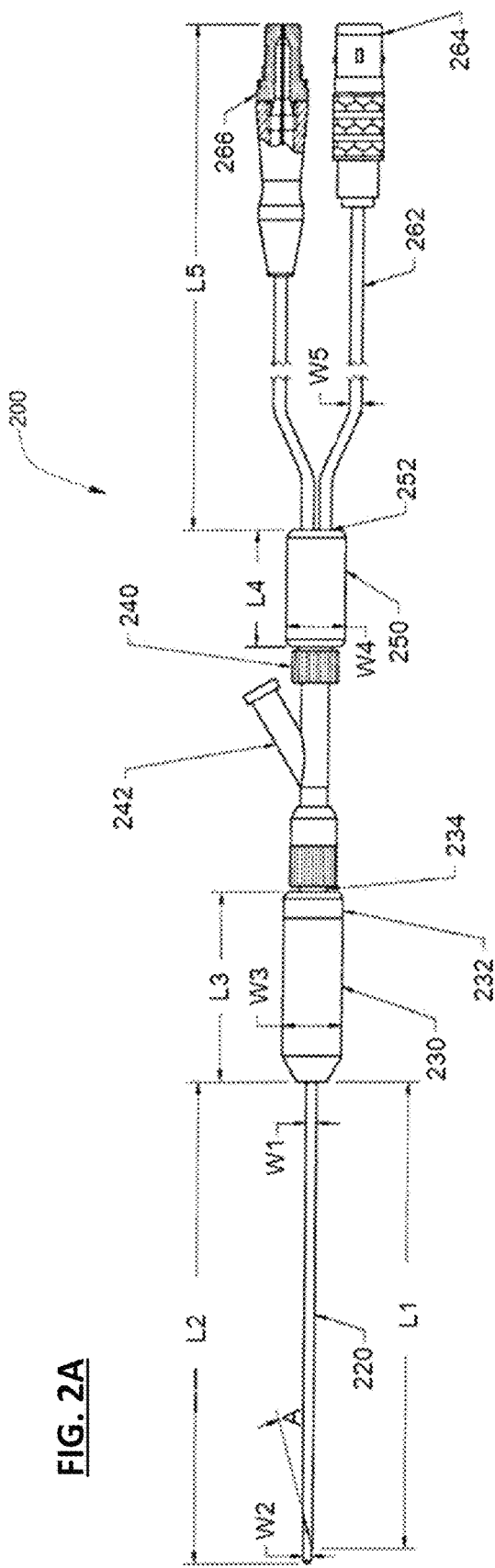
FIGS. 2A-FIG. 2C present various views of a second embodiment in accordance with the present disclosure.

A preferred embodiment of the disclosure, illustrated in FIGS. 1A-1B, acts as a Veress needle to form an incision into a body cavity, as an insufflator to inject gas into the cavity, and as a visualization tool to monitor progress of the Veress needle as it traverses through tissue while progressing toward the abdominal cavity.

Abdominal entry is the most dangerous step of laparoscopic and robotic surgery and is responsible for one patient death—and 8 patient injuries—in the US each day 4.8 million laparoscopic procedures per year are performed in the US. Of these, the vascular injury risk 0.2/1000, the bowel injury risk 0.4/1000, and there is a mortality rate of 13%. There are 2,880 entry related injuries per year, and 374 deaths per year; at least one death per day. Each of these injuries will cost hundreds of thousands of dollars, sometimes millions of dollars, to address. The disclosed embodiments essentially eliminate blind laparoscopic entry, preventing serious patient injuries and death.

For purposes of illustration, and not limitation, as embodied herein and as illustrated in FIG. 1, an apparatus 100 is provided in the form a Veress-type needle. The apparatus 100 includes a handle 110 having proximal end 112 a distal end 114 and a hollow elongate passage 116 therethrough that is in turn connected to a hollow distally extending needle 120 having a sharp distal end 124 for penetrating tissue and that defines a hollow elongate passage 126 therethrough. The passages 116, 126 of the handle 110 and the needle 120 cooperate to form a conduit for passing at least one of fluid or instruments therethrough.

The apparatus 100 further includes a visualization stylet 140 that in turn includes a proximal end 142 and a blunt distal end 144. The visualization stylet 140 is slidably disposed within the conduit (116, 126) of the handle 110 and needle 120. As illustrated, a distal end region of the visualization stylet 140 includes an electronic photodetector chip 146 mounted thereon (or therein) having a distally facing surface 146a including an array of photo sensors that are configured to detect incoming light traveling along a proximal direction (i.e., toward the distal end of the apparatus 100). The apparatus 100 further includes a light source 150, such as a LED disposed in the handle 110, configured to project light beyond the electronic photodetector chip 146 in a distal direction to provide direct illumination of an area being traversed by the apparatus 100. In operation, light originating from the light source 150 traverses the body of the visualization stylet (which can be made from light transmissive plastic, for example) and illuminates the tissue immediately distal to the visualization stylet 140. That light is reflected back to the electronic photodetector chip 146. In accordance with further implementations, one or more fiber optic light transmitting fibers can be used to transmit light from a light source either inside or outside the handle 110 through the device to the distal end of the device. Light may be transmitted using fiber optic fibers down the visualization stylet, and/or the needle 120 and handle 110.

The apparatus 100 still further includes a spring 160 housed within the handle 100 for biasing the visualization stylet 140 (via boss(es)) 147 to extend past the sharp distal end 124 of the needle 120 absent resistance by tissue against the visualization stylet. Thus, in use, while the apparatus is urged against tissue, the visualization stylet urges against the tissue with the needle distal end 124. Once the apparatus traverses the abdominal wall, however, and enters the abdominal cavity, visualization stylet 140 is urged forward by spring 160 beyond the needle distal end 124, thereby preventing the needle 120 from cutting through any additional tissue in the abdominal cavity, including, for example, bowels, blood vessels, and the like.

If desired, the visualization stylet 140 can include a lens element 148 disposed on a distal tip thereof over the electronic photodetector chip 146. Preferably, the lens element can include a solid or hollow piece of plastic, glass, or other suitable material that can be attached to the electronic photodetector chip. In some implementations, the electronic photodetector chip 146 can be integrally molded into a clear plastic body of the visualization stylet 140, wherein a lens is molded over the electronic photodetector chip and further wherein a conductor 148 leading away from the electronic photodetector chip can be directed, for example, along a central axis of the visualization stylet (or the device overall) either embedded in the material of the visualization stylet (via an overmold), or by directing it through a hollow passage (not shown) along the central axis of the visualization stylet 140. If desired, the molding process can result in clear plastic material directly contacting the surface of the electronic photodetector chip.

The visualization stylet can thus be formed from a light transmissive (e.g., transparent or translucent) material such as PET or acrylic, or can be made from other material with one or more fiber optics traversing the length of the visualization stylet to transmit light from the light source. As illustrated, an annular outer area 144a of the distal end 144 of the visualization stylet 140 proximal to the electronic photodetector chip 146 can be provided wherein the electronic photodetector chip is in the middle of the distal end 144 to permit light to be conducted down the visualization stylet, past the electronic photodetector chip 146, and through the lens 148.

As further illustrated, the handle 110 can be provided with a gas introduction port 118 for receiving insufflation gas from a gas source 170. Also, if desired, a flush port 119 can be provided that can direct a liquid in the annular space defined between the handle 110/needle 120 and the visualization stylet 140 to clean the distal end of the visualization stylet. Additionally or alternatively, a flush port can be provided as a parallel lumen structure, indicated by 119a. In some implementations, the visualization stylet 140 is configured to be withdrawn proximally along passages 126, 116 to establish a flow path for the insufflation gas. For example, the visualization stylet need only be withdrawn proximal to the gas introduction port to provide a clear path for directing insufflation gas into the abdominal cavity of a subject.

As mentioned above, the conductor 148 can be provided for directing signals received from the electronic photodetector chip to a second location, such as a processor 180. The processor can thus be coupled to the visualization stylet. The processor can then, in turn, be connected to a display screen 190 for displaying images captured by the electronic photodetector chip 146. The display device 190 can be a large LCD screen that is a part of a separate computer system, or it may be provided as a small local screen attached to the processor and a battery 192 in a module attached to a proximal end 102 of the apparatus, for example. If desired, an adapter (not shown) can be provided to connect the apparatus 100 to a laparoscopic camera, light source and monitor that is available in the operating room.

The disclosure further provides a method of using an apparatus as described herein to more safely accomplish an insufflation procedure in preparation for a laparoscopic surgical procedure in the abdomen. The method includes puncturing a surface of skin of a subject with a sharp distal end of a hollow needle (e.g., 124) of the apparatus (e.g., 100). The method further includes advancing the distal end of the hollow needle (e.g., 124) through successive layers of the abdominal wall of the subject while viewing the tissue being advanced through via the visualization stylet in real time. The process still further includes stopping advancement of the distal end of the hollow needle when reaching the abdominal cavity. A user can note that the abdominal cavity has been reached when the visualization stylet shoots distally under force of the spring 160 past the distal end 124 of the needle 120. At this point, the visualization stylet 140 can be retracted proximally, such as under manual action, and the method can further include commencing insufflation through the hollow needle.

Figure 2B:
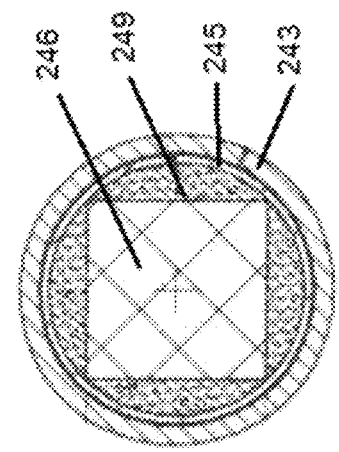
Figure 2C:
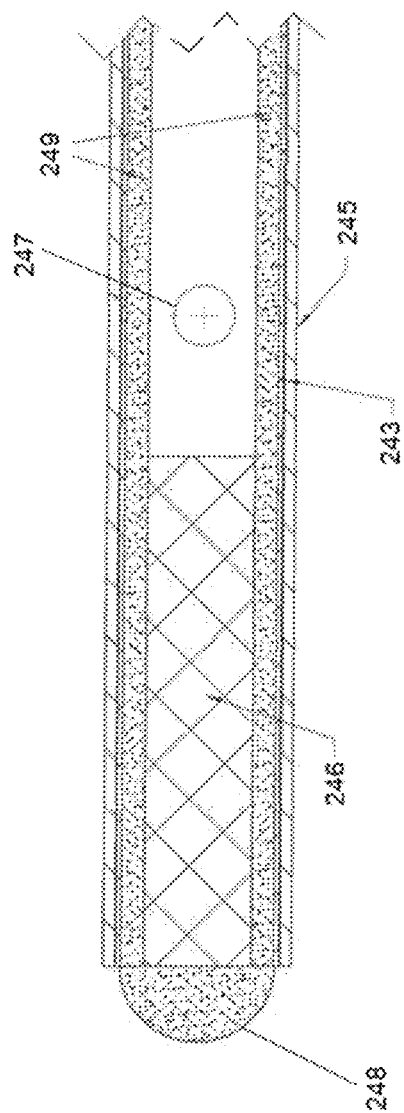

In further accordance with the disclosure, a second embodiment of a visualization insufflation needle assembly 200 is presented in FIGS. 2A-2C. With reference to FIG. 2A, the assembly includes an outer sheath 220 with an angled, sharpened distal tip for penetrating tissue, including a spring loaded visualization stylet, similar to that in FIGS. 1A-1B. The outer sheath can be made, for example, from stainless steel tubing, and have a length L1 between for example, about 2 and about 6 inches, in increments of about one eighth of an inch. Visualization stylet can have a similar length L2. The diameter, or width, W2, of the visualization stylet can be, for example, between about 0.050 to about 0.1 inches in increments of 0.01 inches. The sheath can have a diameter or width W1 between about 0.06 and 0.12 inches, in increments of 0.01 inches. The distal tube 220 is attached at a proximal end to a cannula body 230 with a cannula cap 232 that may be removable. A spring biasing mechanism similar in functionality to that illustrated in FIG. 1A is contained within cannula body 230 that is operably attached to the visualization stylet for biasing it beyond the tip of the outer tube 220. Cannula 230 can have a length L3 between, for example, about 1.5 and 2.0 inches, in increments of one sixteenth of an inch, and a width or diameter W3 between about 0.4 and 0.8 inches, in increments of about 0.05 inches. The proximal end of cap 232 is adjacent to a female Luer lock connector 234 with a Y connector 242 and proximal male Luer lock connector 240. Connector 240 is received by an electronics connector 250 having a proximal plug 252 that in turn connects to a light source 266 for directing light down the visualization stylet to provide illumination and to a camera output connector 264 for directing digital image data to a processor and/or screen. If desired, connector 264 can include specialized circuitry specifically configured for converting data received from the photodetector in the visualization stylet into a video output signal. Sheathing 262 is provided for protecting the video output cable. Body 250 can have any suitable length L, for example, between about 0.75 and 2.0 inches in increments of 0.1 inches and a diameter or width W4 between about 0.4 and 0.8 inches, in increments of about 0.05 inches. Length L5 can be between, for example, 8 and 24 inches or in any increment therebetween of about one quarter inch.

FIGS. 2B and 2C present end and cross sectional views of the distal end region of the visualization stylet. FIG. 2B shows a view of the distal end with the lens 248 removed, thereby illustrating the photodetector array 246 and surrounding structures. Light is transmitted distally through illumination bundle 249 which surrounds the photodetector array 246. Illumination bundle is in turn surrounded by a polymeric illumination sheath 243, made for example of a suitable polymer such as polyimide. A transverse opening 247 is provided for permitting insufflation gas passing down the hollow bore of the visualization stylet to pass through the outer wall of the visualization stylet for insufflation of the peritoneum. Conductors (not shown) are connected to array 246 to conduct data indicative of light received by the array proximally and out of device 200. Sheath 243 is in turn surrounded by a (preferably metallic) tubular member 245 that is attached at its proximal end to a spring that is also attached to cannula body 250.

The visualization stylet, particularly the distal end region of the visualization stylet, can be made in a variety of ways and having a variety of features. FIGS. 3-11A illustrate cross sectional views of different embodiments of this portion of the device (e.g., 100, 200) that include like reference numbers for similar structures.

Figure 3:
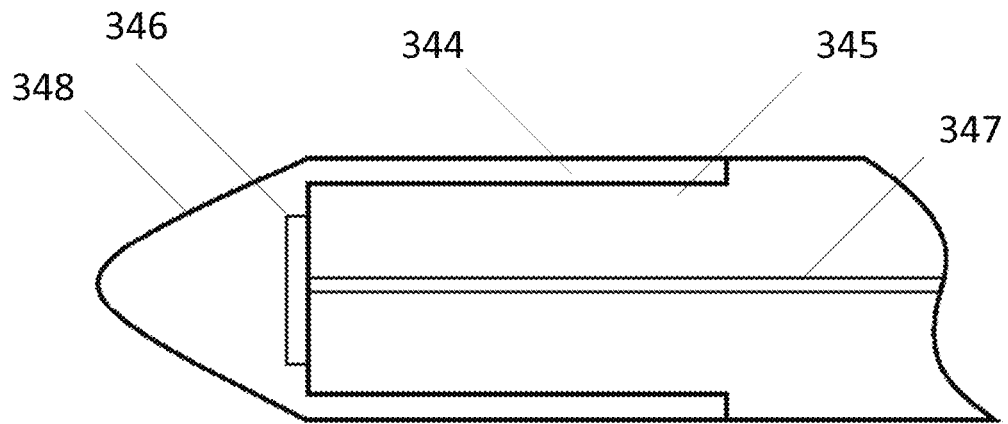
FIGS. 3-10 present various embodiments of visualization stylet distal tip and lens configurations in accordance with the present disclosure.
Figure 4:
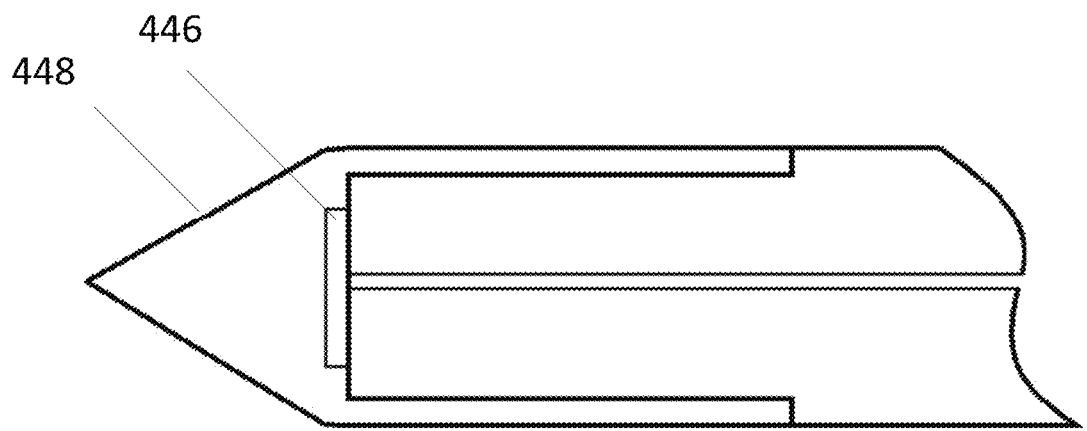

FIG. 3 illustrates such a distal region having a distal lens cap 348 that is substantially conically shaped with a curved tip that can be useful for blunt dissection. The cap is defined by a solid or hollow end region that can be a conic section, for example, that transitions into an annular tubular region that is slidably received, for example (and adhered or otherwise attached to) a recessed portion 345 of a main body portion of the visualization stylet, which in turn includes a photodetector array 346 (shown in simplified form). Illumination bundles and other structures similar to the embodiment of FIGS. 2B-2C can also be provided. One or more central passages 347 can also be provided to accommodate the passage of data conductors or the passage of liquid or gaseous flushing fluids for irrigating the tip of lens 348, as desired. FIG. 4 illustrates a distal end region that alternatively includes a sharp conical, or pyramid (e.g., 3, 4, 5, or 6 sided) shaped lens 448.

Figure 5:
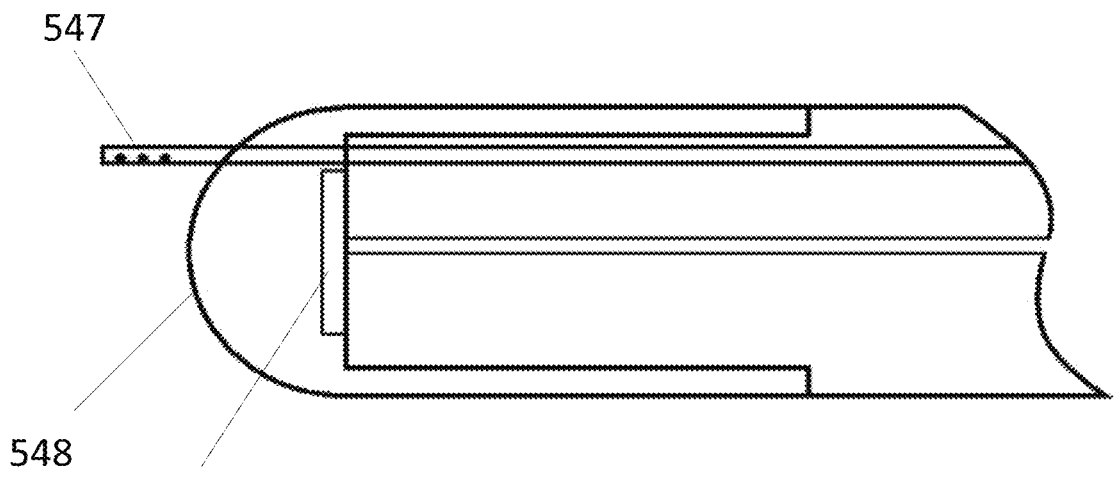

FIG. 5 is similar to the embodiments of FIGS. 3 and 4, but includes a dome shaped lens 548, and photodetector 546 and the like. Additionally, the embodiment of FIG. 5 includes a first embodiment of a lens flushing mechanism that includes a tubular body 547 directed through the body of the visualization stylet that includes a plurality of flushing holes. The body 547 can be formed from a hypotube, for example, with a sealed distal tip and one or more transversely formed holes through the hypotube to direct a fluid jet across the lens, wherein the fluid can include, for example, saline, another liquid and/or a gaseous substance, such as carbon dioxide insufflation gas. Tube 547 is preferably slidably movable with respect to visualization stylet, and can be controllably deployed by advancing it distally with respect to the visualization stylet distal tip. In one embodiment, the tube 547 is made from a shape memory material (e.g., Ni Ti alloy) wherein it is heat set to bend around the tip to direct cleaning liquid and/or gas at the tip along a direction that is partially transverse and partially axial in a proximal direction. The tube 547 can still be retracted proximally into a straight guide channel. If desired, more than one such tube 547 (Ni Ti or other material) can be provided at various locations to effectuate efficient cleaning. In further embodiments of devices and methods (not illustrated), a mechanical wiping seal or wiping pad is provided inside the cannula or sheath for wiping off the distal tip of the visualization stylet.

Figure 6:
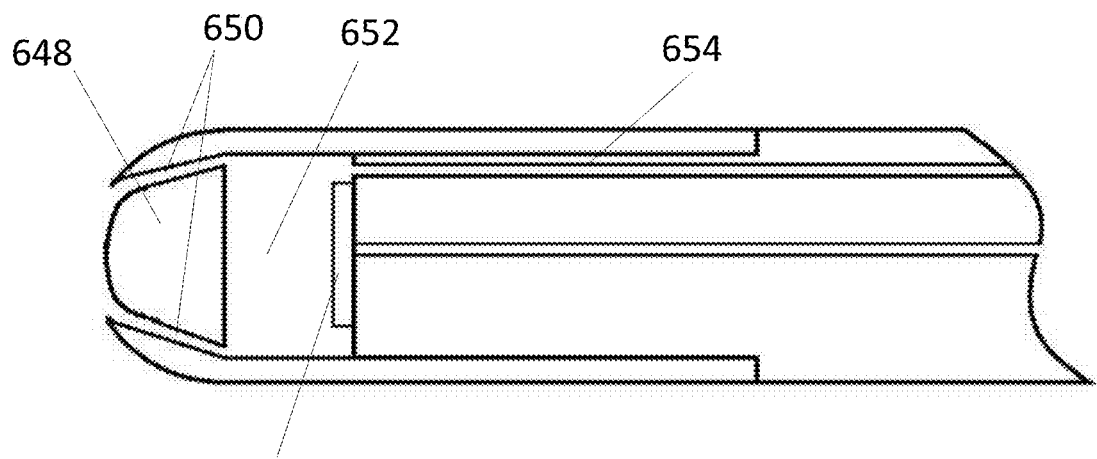

FIG. 6 illustrates an embodiment similar to that of FIG. 5, wherein that a cavity 652 is provided between the distal tip of the photodetector array and the distal lens 648. If desired, a flush channel 654 can be provided for directing liquid and/or gas into cavity 652 for enhancing optical performance. In such an instance, a small vent hole can be provided. Moreover, if desired, one or more circumferentially located flush channels 650 can be provided that pass through the lens 648. If desired, in some embodiments, such flush channels can be distributed across the surface of the tip to help keep it clean. Preferably the index of refraction of the flushing fluid, e.g., a liquid, is matched to that of the material of the tip to minimize image distortion. Furthermore, if desired, the tip of the central region of the lens can be located proximally with respect to the circumference of the lens. This permits, as shown, flush passages that vector flushing fluid (liquid and/or gas) over the face of the central portion of the lens 648. Moreover, it will be appreciated that the flush passages do not necessarily need to be directed radially inward, or at least not significantly, in order to obtain a cleaning benefit. Specifically, Applicant believes that suitably configured cleaning passages and suitable flow rates for liquids (e.g., saline) and/or gases (e.g., carbon dioxide) will result in cleaning fluid streams that hug the surface of the lens, even as it curves toward the distal tip. This is known in fluid mechanics as the "Coandă effect". Specifically, the Coandă effect is the phenomena in which a jet flow attaches itself to a nearby surface and remains attached even when the surface curves away from the initial jet direction. Thus, it is possible to have the benefits of cleaning passages while minimizing their effect on reduction of field of view of the lens, and/or image distortion through the lens. Thus, for example, a liquid stream can be ejected through the cleaning passages and followed by a burst of gas flow. Alternatively, simply a gas flow can be used through the passages.

If desired, the distal tip can be formed by fitting a separate lens 650 into the circumferential region. This can be done, for example, by attaching the lens center 650 to the photodetector 646 or to the light transmitting bundles surrounding it, by extending the proximal face of the lens central region so that it abuts the photodetector and/or surrounding area. In that instance, the annular outer portion of the lens can be provided in the form of a separate tubular member that slips over the center region of the lens. If desired, in that instance, the lens center 650 and/or the peripheral region can be provided with standoffs, preferably that are circumferentially disposed (preferably three, but other amounts can be used), to separate and align the inner central portion of the lens 650 with the annular outer portion, and also to define the flow path for the flush channels.

Figure 7:
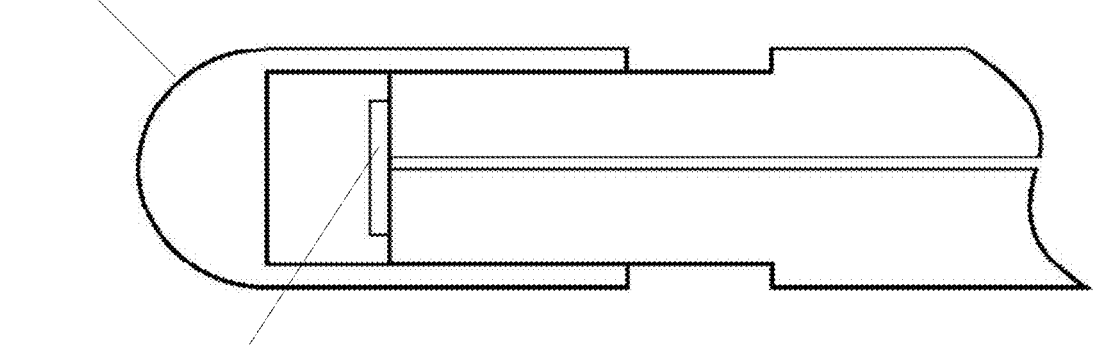
Figure 8:
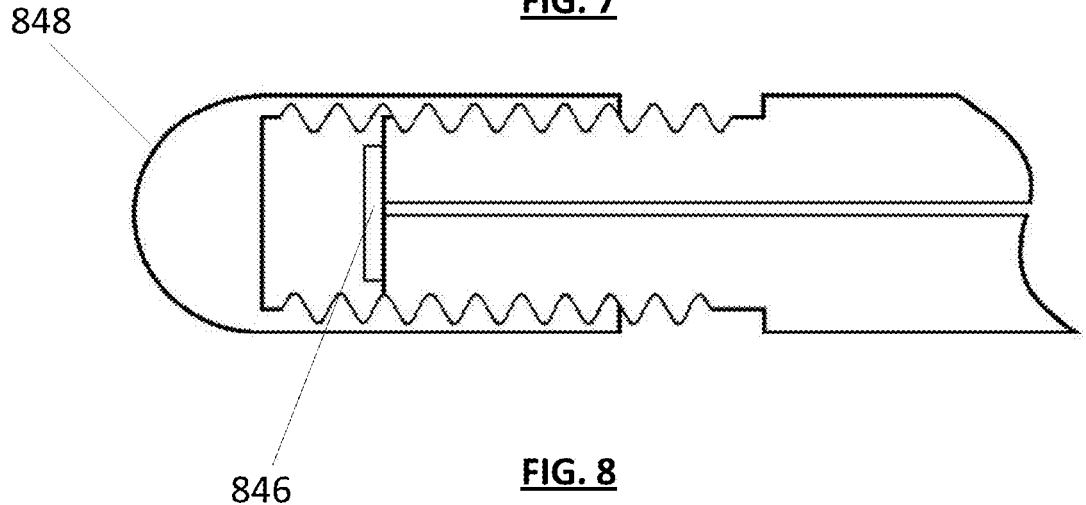
Figure 9:
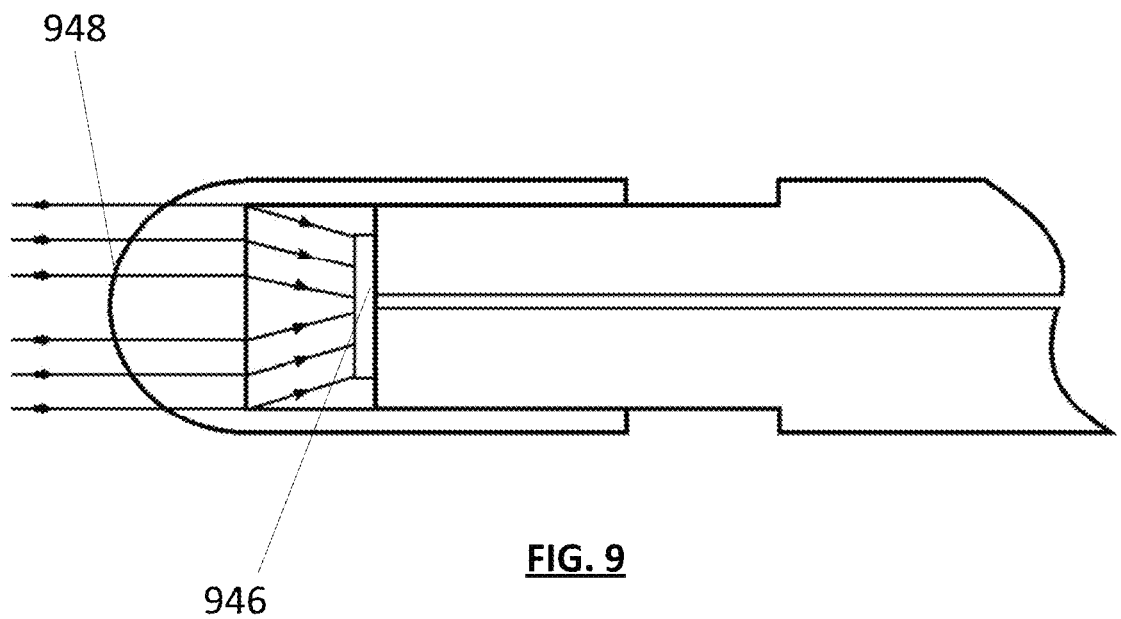
Figure 10:
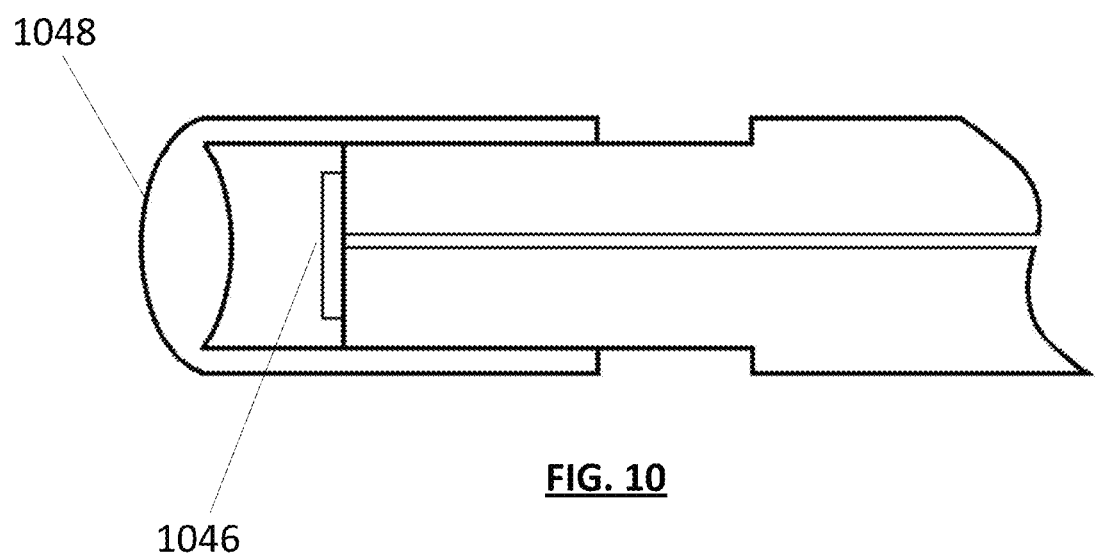

FIG. 7 illustrates a further embodiment wherein the lens 748 is slidably mounted on the visualization stylet to permit adjusting the axial distance between the lens and the photodetector 748 to accommodate for focal length of the lens. This can be accomplished by an interference fit that is adjustable, or by way of a push pull actuation arrangement discussed below with respect to FIGS. 12A-12B. FIG. 8 shows an alternative focal length adjustment arrangement that utilizes a screw thread connection between the lens 848 and the body of the visualization stylet to adjust the axial distance between the lens and photodetector 846. FIG. 9 illustrates a ray diagram showing the lens 948 in the form of a plano-convex lens that is configured to focus incoming light radially inwardly on the photodetector 946. FIG. 10 illustrates a similar arrangement for a convex lens. The curvature of the lens (or lack thereof) can be selected to accommodate narrower or broader fields of view.

Figure 11A:
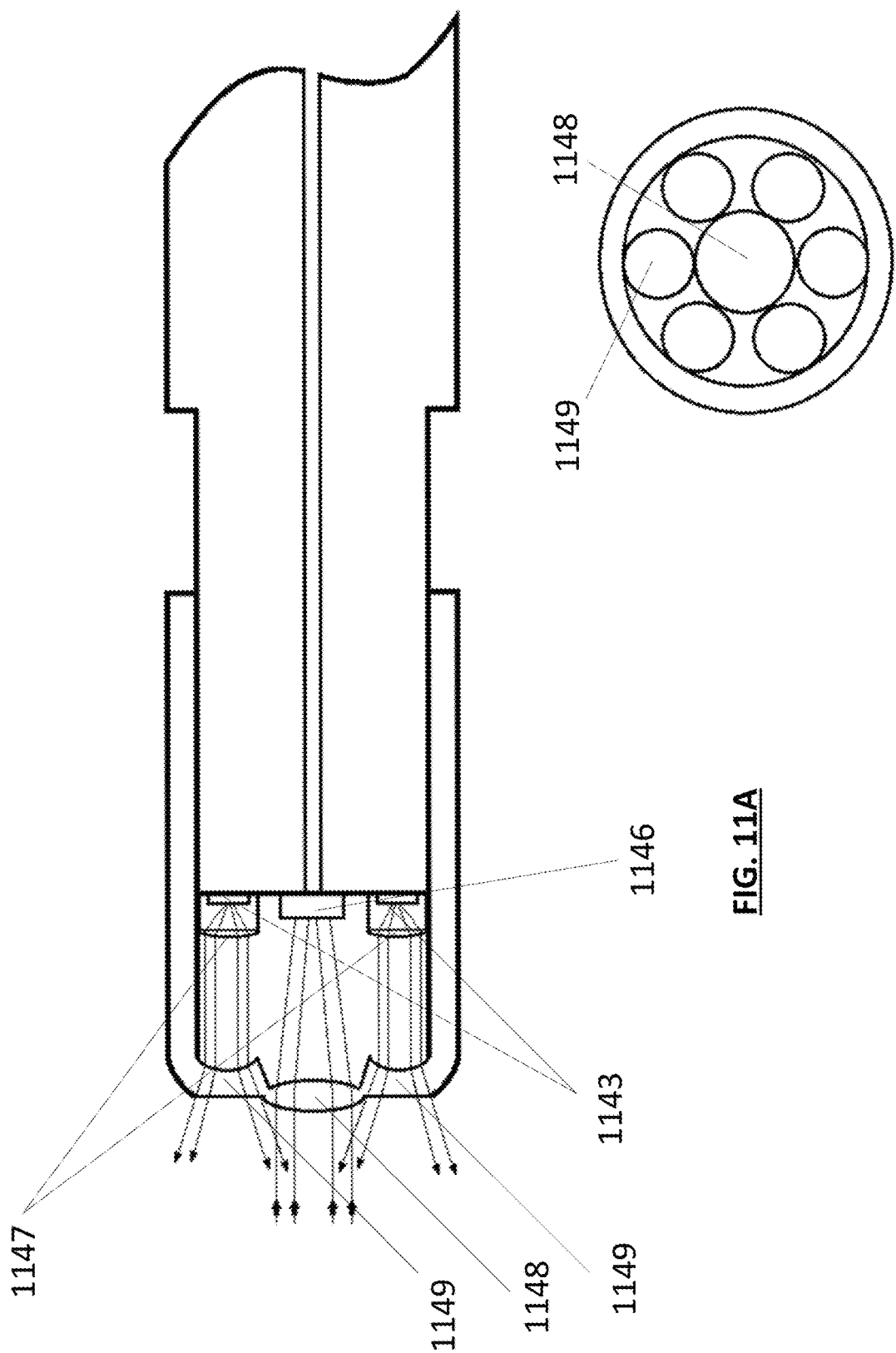
FIGS. 11A-FIG. 11B present various views of a further embodiment of visualization stylet distal tip and lens configuration in accordance with the present disclosure.
Figure 11B:
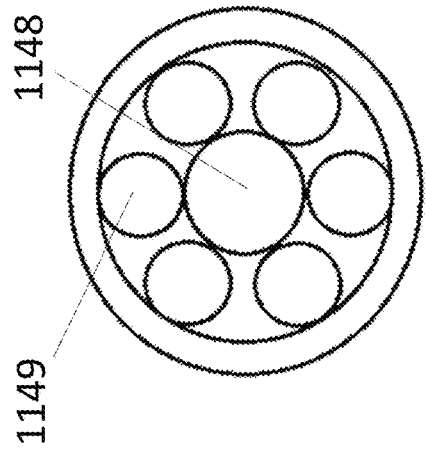

FIGS. 11A and 11B illustrate a more complex lens arrangement wherein light being delivered for purposes of illumination goes through one or more separate lenses from the lens used to collect incoming light onto the photodetector 1146. Specifically, the lens can be a molded lens assembly having, for example, a central portion 1148 that is a convex lens (or other lens) for collecting light and focusing it on the photodetector 1146, and one or more (e.g., 2, 3, 4, 5, 6) circumferentially arranged smaller lenses 1149 for distributing light from the light bundle outwardly. Preferably, the optics are arranged to minimize internal reflections in the lens and reduce the mixing of outgoing and incoming light. If desired, the light source can include micro-LEDs 1143 that are mounted underneath a suitable optic, or lens, 1147, having optics matched to deliver light out of secondary lenses 1149. If desired, the electronic photodetector chip and micro-LEDs can be formed on the same chip or circuit board and have optics molded thereover to simplify manufacture.

Figure 12A:
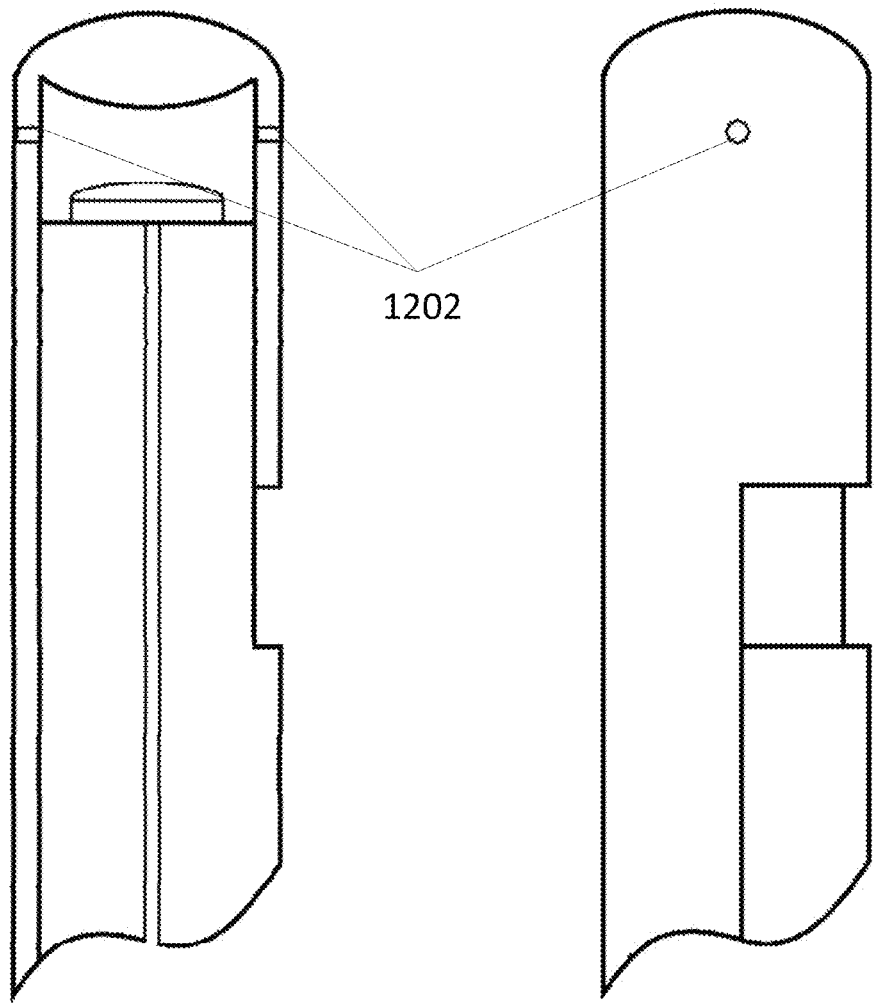
FIGS. 12A-FIG. 12B present a cross sectional and side view, respectively of a further embodiment of visualization stylet distal tip and lens configuration in accordance with the present disclosure.
Figure 12B:
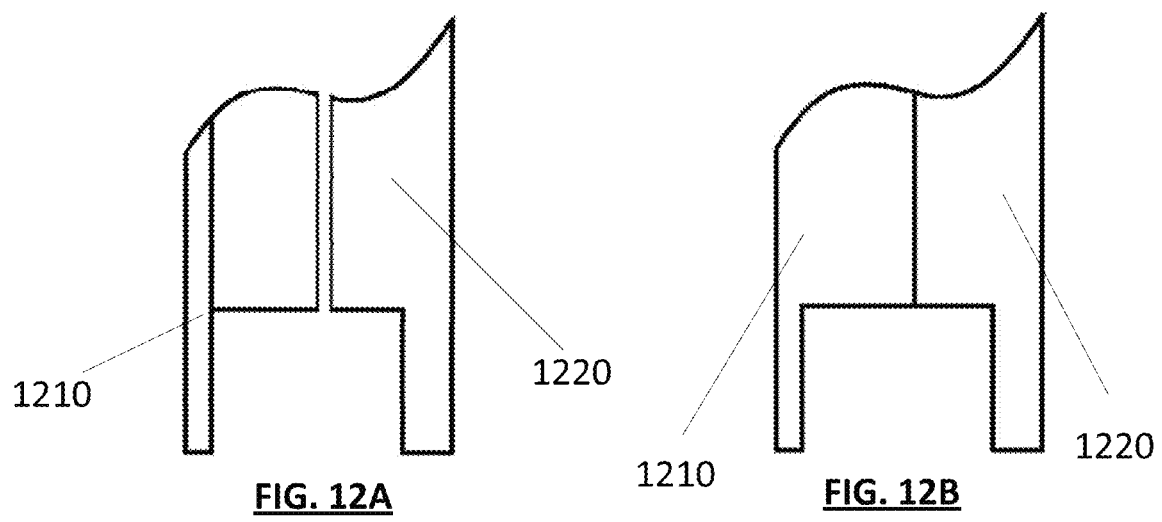

FIGS. 12A-12B illustrate an embodiment of an visualization stylet that has a push-pull actuator for adjusting the axial distance between the lens and the photodetector. For example, a first portion of the actuator 1210 is connected to the distal lens, and a second portion 1220 is attached to the central portion of the visualization stylet. The axial length can be accomplished, for example, by a simple push pull arrangement. Or, if more precision is required, an actuator using a screw thread can be used for a finer adjustment. Vent holds 1202 can be provided to permit liquid or other fluid to flow into or out of the cavity space between the lens and the photodetector. It will be appreciated that such vent holes can be provided in any embodiment herein.

Figure 13A:
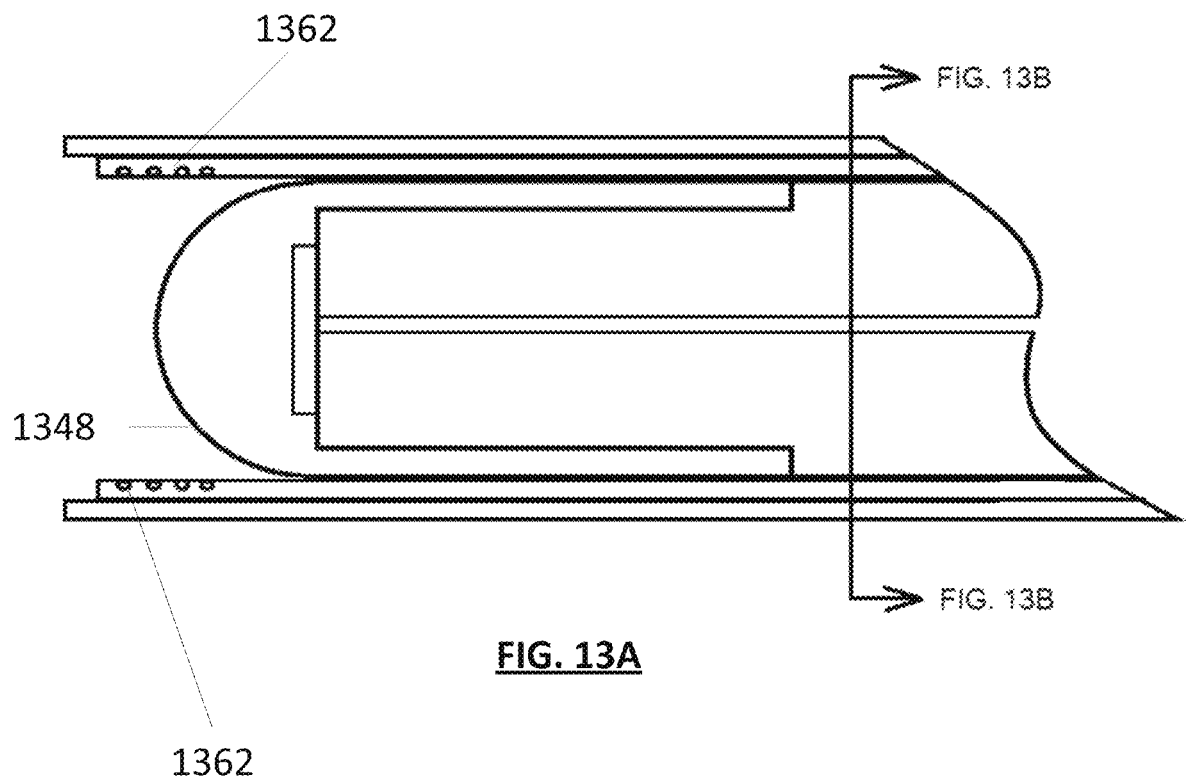
FIGS. 13A-FIG. 13B present a cross sectional and end view, respectively of a further embodiment of a device in accordance with the present disclosure that is configured to facilitate cleaning of a distal tip of the visualization stylet.
Figure 13B:
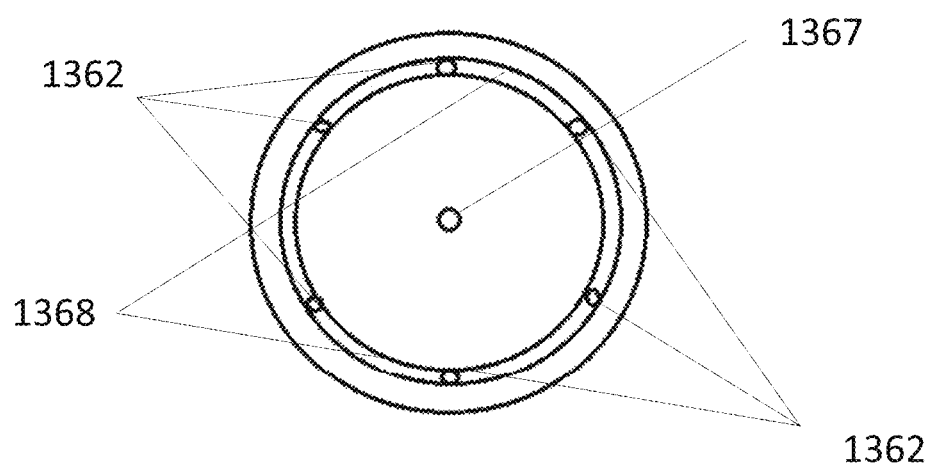

FIGS. 13A-13B illustrate a further embodiment of a visualization Veress needle that incorporates flushing pathways or conduits into the sheath of the needle that surrounds the visualization stylet. As depicted, preferably 3, 4, or 6 longitudinal channels 1362 are provided (such as small hypotubes) that are attached to the inner surface of the sheath (e.g., 220). These tubes 1362 act to evenly space the visualization stylet from the outer sheath, and cooperate with the outer tube and visualization stylet to define longitudinal passages 1368 for the passage of insufflation gas, or simply to reduce friction. As illustrated, the distal tip of tubes 1362 can be sealed, and laser drilled holes can be formed that are transverse to the visualization stylet, such that cleaning fluid directed through the tubes 1362 will be directed transversely across the distal tip of the visualization stylet to clean the lens 1348. Visualization stylet can be moved proximally and distally with respect to the outer sheath when cleaning to facilitate cleaning during a cleaning process.

FIGS. 14A-14C illustrate an embodiment of a visualization Veress needle that can be taken apart to facilitate different procedures. For example, 14A illustrates a distal portion of a Veress needle, such as that illustrated in FIGS. 2A-2C, having an visualization stylet 1406 that is connected to an outer sheath 1402, wherein sheath 1402 is removably connected to a cannula 1404 that provides insufflation gas. After insufflation, portion 1404 can be removed from portion 1402 (e.g., by a screw threaded connection 1409), and a new proximal portion 1408 can be attached to threads 1409 to use the assembly as a laparoscope. If desired, the visualization stylet 1406 can be removed from the assembly of 1402 and 1404 (e.g., by detaching a screw threaded connection). A seal (not shown) inside of component 1402 or 1404 can be provided to prevent the loss of insufflation gas.

FIGS. 15A-15C illustrate a system and method for separating the visualization stylet 1506 from an outer cannula 1504, such as by disconnecting a threaded connection. After the assembly is inserted under visualization into the peritoneum, the visualization stylet can be removed, if desired, leaving the outer sheath in place as a cannula. Or, the outer sheath can be removed, permitting an extension 1508 to be attached to visualization stylet 1506 to effectively use visualization stylet 1506 as a laparoscope. If the visualization stylet is removed, a seal (not shown) can be provided within the body of the cannula 1504 to prevent undue loss of insufflation gas and to maintain pressure in the peritoneum. Visualization stylet can be removed, for example, to remove the lens cap (e.g, 148 et. seq.), permitting the visualization stylet to be reintroduced without the lens cap. In a further embodiment of a method, the lens is hinged to the end of the visualization stylet and can swing out of the way by actuating an actuator.

Figure 16C:
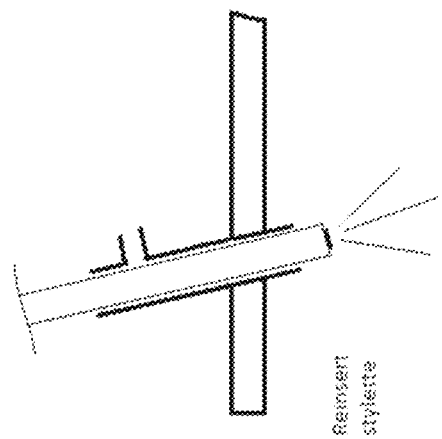
FIGS. 16A-FIG. 16C present views of steps of yet another method in accordance with the present disclosure.
Figure 16B:
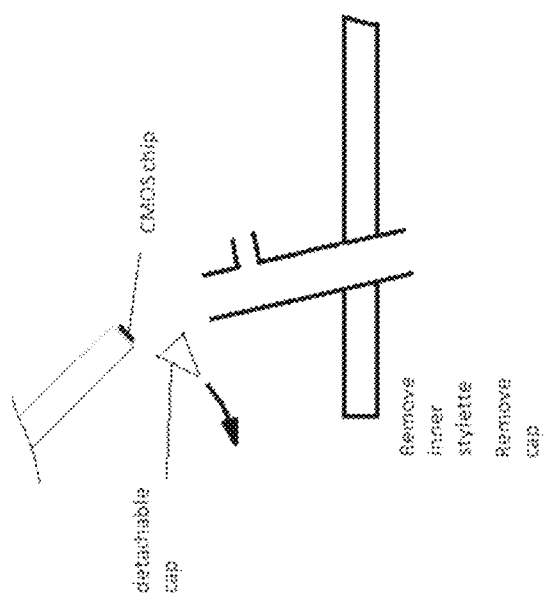
Figure 16A:
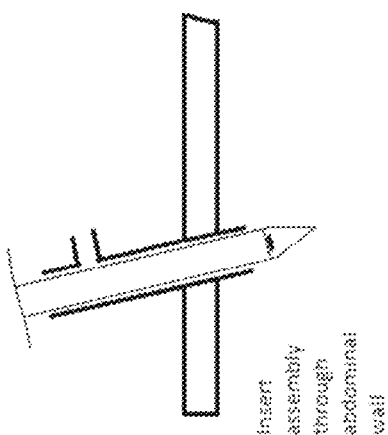

FIGS. 16A-16C illustrate a further system and method for separating a visualization stylet from an outer cannula that is used to insufflate the peritoneum. The outer cannula includes an insufflation port to receive an insufflation gas input. After the assembly is inserted under direct visualization into the peritoneum in FIG. 16A, the peritoneum can be insufflated, and the visualization stylet can be removed as indicated in FIG. 16B. The inner stylet can include a CMOS chip at its distal end as discussed elsewhere herein that can be covered by a removable distal cap or cover. The removable distal cap or cover can have a sharpened tip or a blunt dissection tip of any desired shape (e.g., conical, pyramidal, etc.) and any additional features that are desired (e.g., ridges or wings or tabs extending outwardly from the removable tip). The tip can thus be removed, and the inner stylet can be replaced into the outer cannula to perform an illumination and/or visualization function. Removal of the tip can be helpful as the tip can become obscured during the initial insertion process. If desired, a different tip can be added to re-cover the CMOS chip, or the CMOS chip can have a lens that is covered by the removable distal tip. The outer cannula can continue to direct carbon dioxide into the peritoneum.

In further accordance with the disclosure, FIGS. 17A-18N illustrate a further embodiment of a visualization trocar assembly in accordance with the present disclosure.

FIG. 17A is an isometric view of an optical trocar assembly 1700 in accordance with the present disclosure. FIG. 17B is a close up view of a distal end portion of device 1700. As depicted, device 1700 includes a proximal handle portion 1750 that may be removably coupled to a distal cannula 1710. Distal cannula 1710 includes a proximal handle portion that is coupled to a distal shaft 1712. Shaft 1712 is hollow, has a distal end portion 1714, and is configured to receive an elongate removable sheath 1720 therein. An annular gap can be defined between the inner surface of the lumen defined through the shaft 1712, and the external surface of the sheath 1720. A flushing assembly 1760 is provided that includes an input port, a valve, and an output port that directs liquid or other beneficial agent to a cavity defined between the cannula 1710 and the handle 1750, resulting in fluid being directed between shaft 1712 and sheath 1720, or between shaft 1712 and optical probe 1780, discussed below, when the sheath 1720 is removed. As illustrated, the sheath 1720 of embodiment 1700 can terminate in a dissecting tip 1724 that can include one or more ridges or wings that can help bluntly dissect tissue that it is pressed against. If desired, the tip 1724 can be sharpened to the extent needed to help it traverse tissue. As will be appreciated, while the shaft 1712 can be any desired diameter, in the illustrated embodiment, the shaft has an outer nominal diameter of about 2 mm.

Figure 17C:
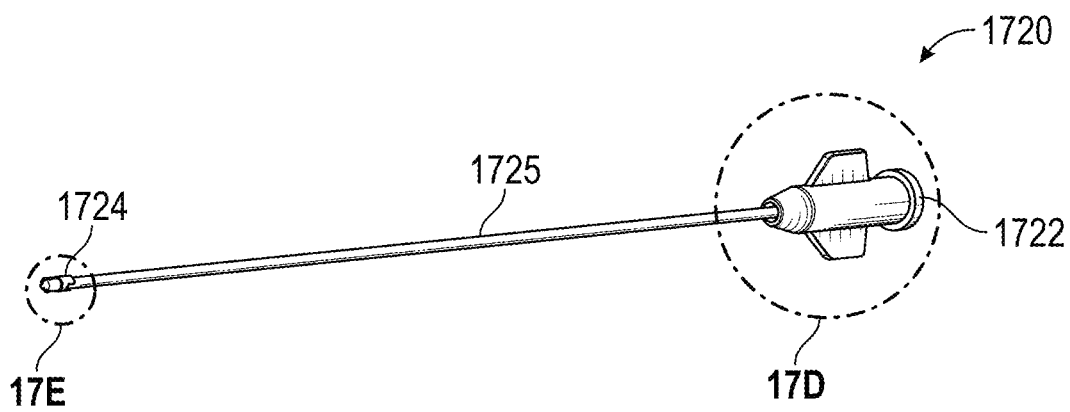
FIGS. 17C-17E are views of a removable sheath of the device of FIG. 17A.
Figure 17D:
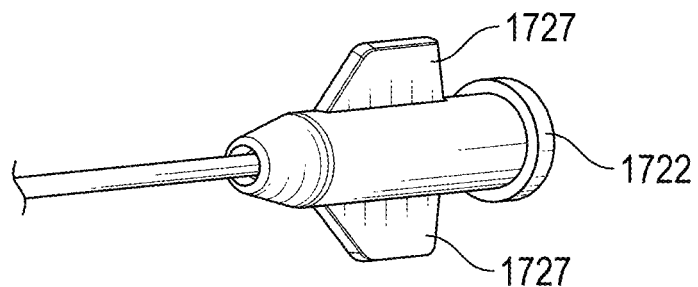
Figure 17E:
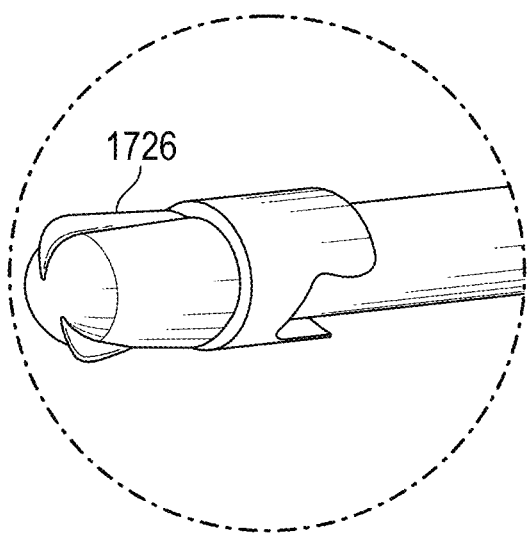

FIGS. 17C-17E are views of a removable sheath of the device of FIG. 17A. As illustrated, sheath 1720 includes an elongate tubular member 1725, made, for example, from a metallic material as with shaft 1712. Sheath 1720 includes a female luer lock, or other coupling, 1722 at a proximal end thereof, and includes distal tip 1724 coupled to a distal end thereof. In FIG. 17E, an alternative embodiment of a tip is shown having a pair of opposing wing portions 1726. The tip is at least partially transparent, and can include one or more masked portions to render part of the tip opaque, such as by screen printing, as desired, to remove optical artifacts resulting, for example, from wings 1726 or other geometric feature.

FIGS. 18A-18K illustrate a process of removing the sheath 1720 from the device 1700. In use, Applicant has come to appreciate that optical trocars can easily become dirty or otherwise obscured during the initial process of directing the device into the body.

Figure 18A:
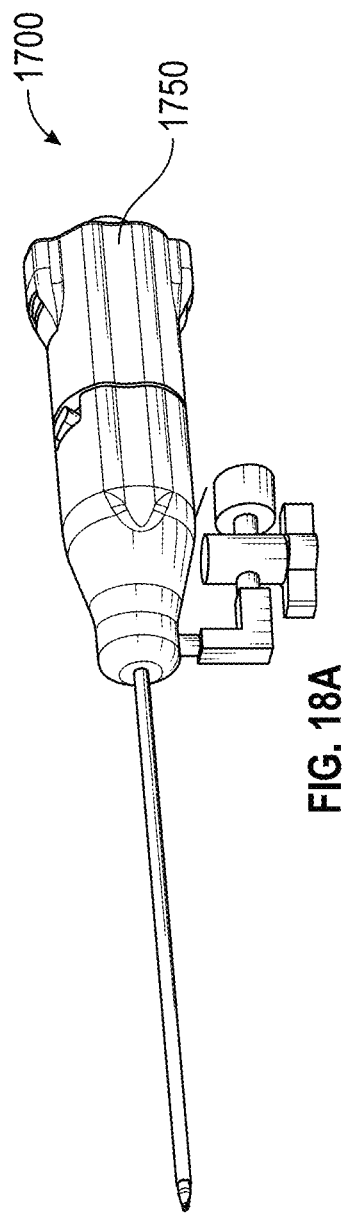
FIG. 18A is a view of the device of FIG. 17A prior to separating components to remove the sheath from the device.

FIG. 18A is a view of the device 1700 prior to separating components to remove the sheath 1720 from the device. This may be done after the device 1700 has been inserted, for example, into the peritoneum of a patient. During insertion, the optical tip 1724 can be expected to become obscured. Thus, the proximal portion of the device may be removed, the sheath can be removed from the proximal portion of the device, uncovering the optic or stylet, 1780, and the stylet can be reinserted into the cannula, permitting a clear view of what is inside the patient.

Figure 18B:
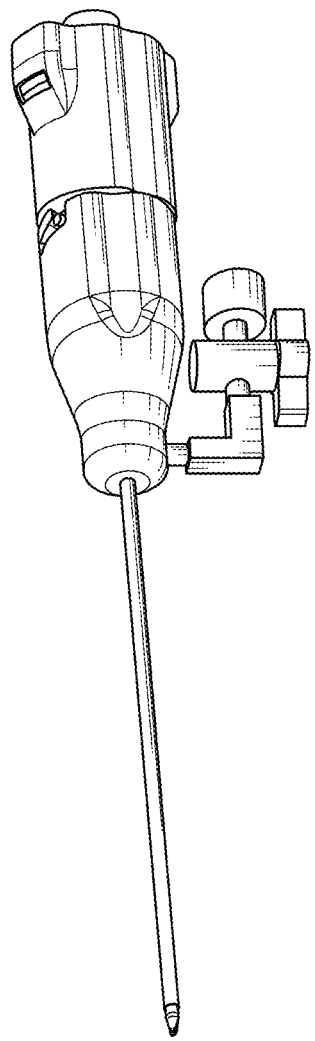
FIG. 18B is a view of the device of FIG. 17A after rotating a handle portion of the device with respect to a cannula portion of the device.
Figure 18C:
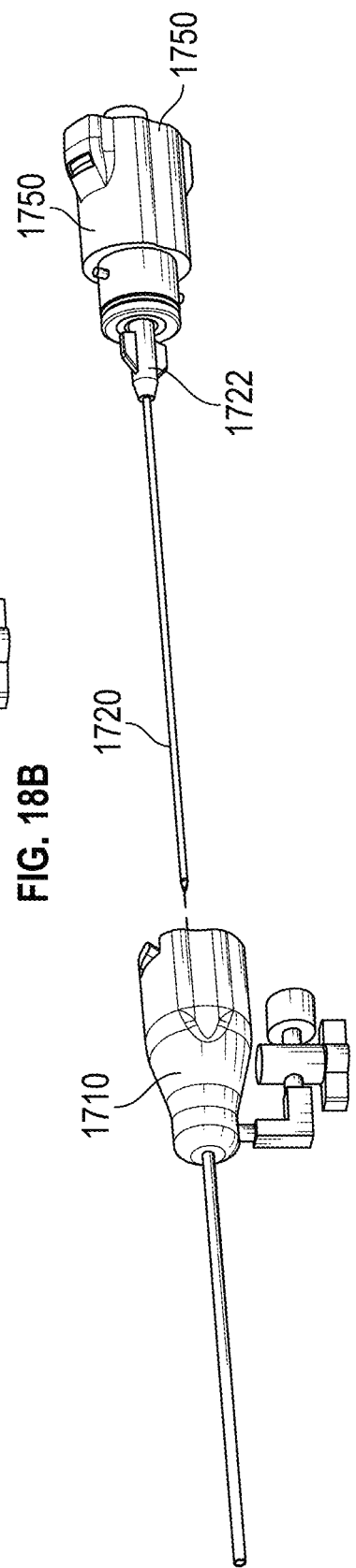
FIG. 18C is a view of the device of FIG. 17A after withdrawing an assembly of the handle portion with the sheath attached thereto from the cannula portion of the device.
Figure 18D:
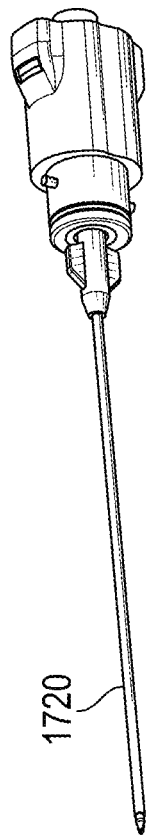
FIGS. 18D-18G illustrate a sequence of steps of rotating the sheath with respect to the handle portion of the device and removing the sheath portion from the handle portion (FIG. 18G).
Figure 18E:
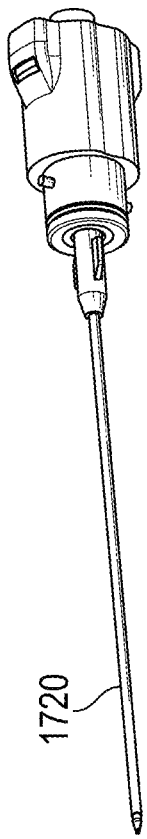
Figure 18F:
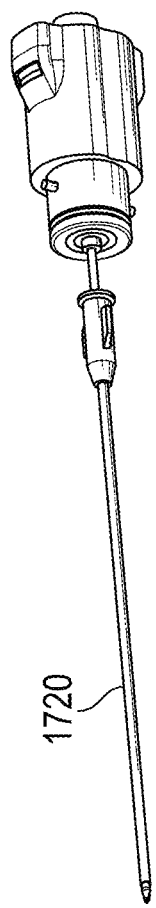
Figure 18G:
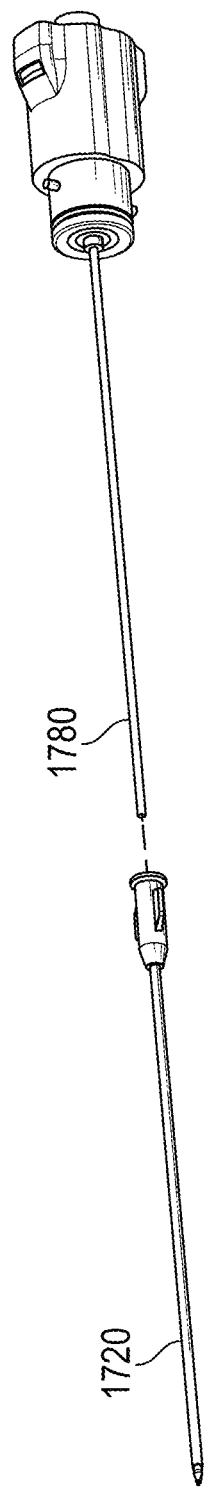
Figure 18H:
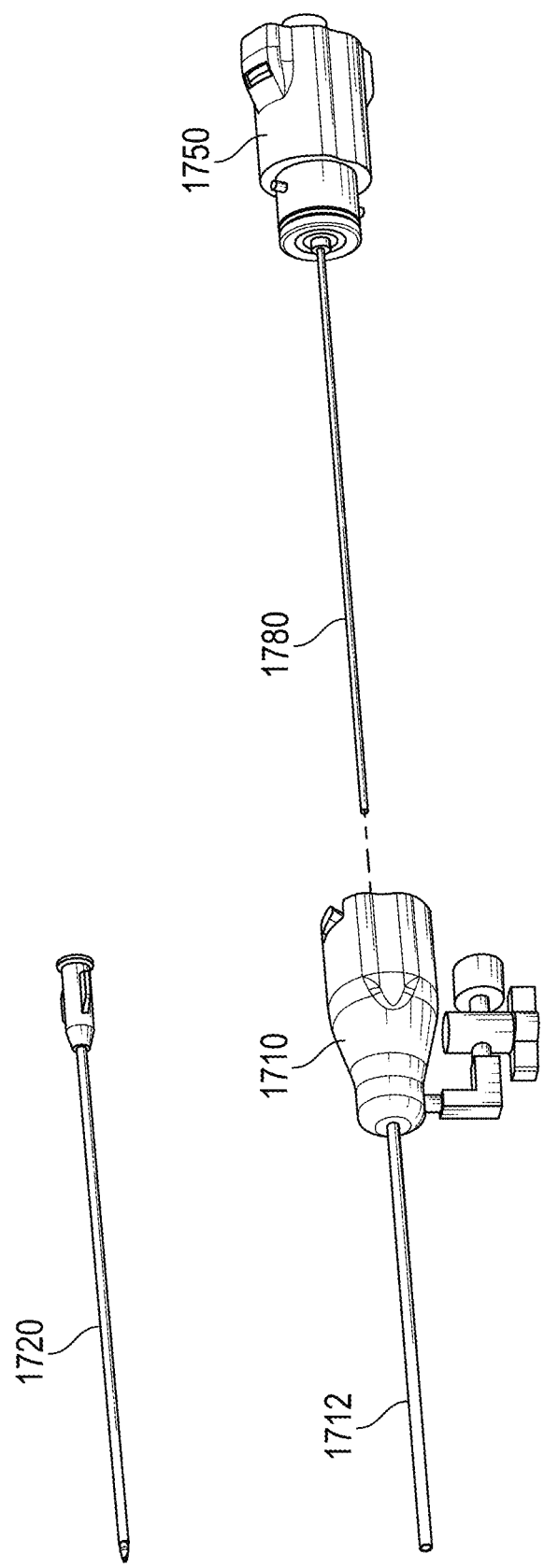
FIG. 18H is a view showing relative placement of the cannula, sheath and handle after the sheath has been removed.

FIG. 18B is a view of the device 1700 after rotating handle portion 1750 of the device counter-clockwise with respect to a cannula portion of the device to release the "J" connector that connects the two components. With the "J" connector uncoupled, the handle bearing the sheath 1720 may be withdrawn in a proximal direction as illustrated in FIG. 18C, and the cannula 1710 can be left in place in the patient. With the proximal portion of the assembly 1750 withdrawn, it is now possible to remove the protective sheath 1720 from the optic/scope/stylet 1780. With reference to FIGS. 18D-18G a sequence of steps is illustrated, including of rotating the sheath proximal end connector 1722 with respect to the handle portion of the device 1750 to decouple the luer lock of the sheath from the connector at the distal end of the handle portion 1750. The sheath in this embodiment is composed of the luer connector at the proximal end, and an elongate shaft 1725, that terminates in a distal tip that is optically clear. This sheath 1720, once removed, exposes the CMOS sensor at the distal end of the stylet 1780 as set forth in FIG. 18G. FIG. 18H is a view showing relative placement of the cannula, sheath and handle after the sheath has been removed.

Figure 18I:
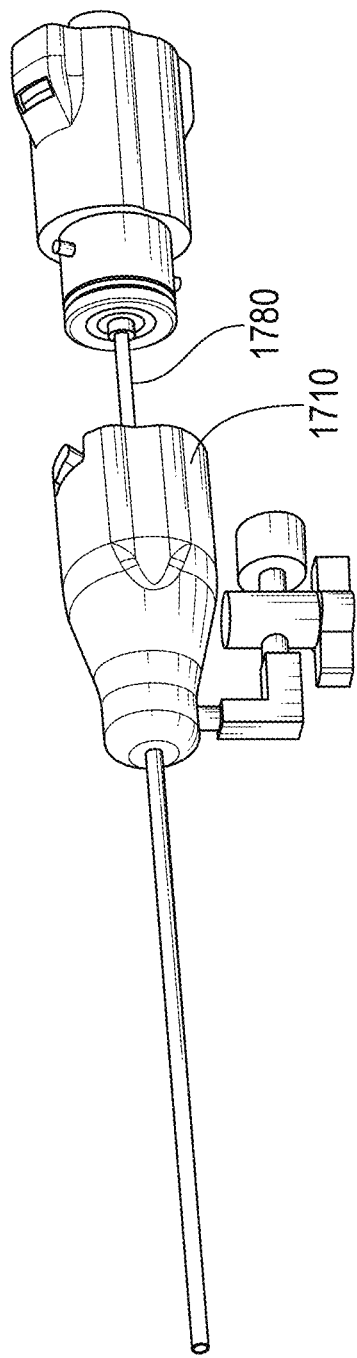
FIGS. 18I-18K illustrate reinserting the handle with the optical shaft into the cannula after having removed the sheath.
Figure 18J:
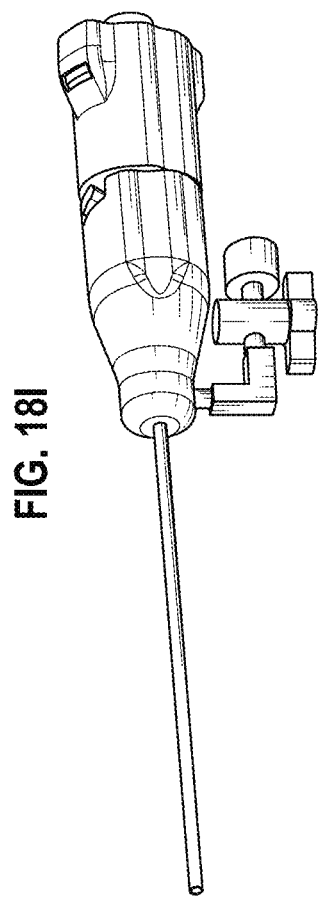
Figure 18K:
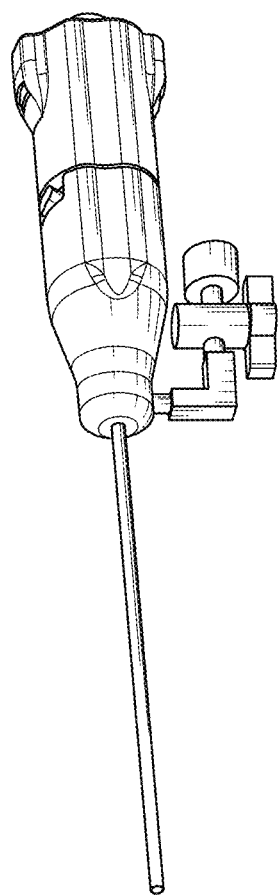

FIGS. 18I-18K illustrate reinserting the handle with the optical shaft into the cannula after having removed the sheath. As can be seen, the stylet 1780 is reinserted into the cannula 1710, and the "J" connector is reconnected. At this point, the overall assembly can be maneuvered about to view different tissue structures.

Figure 18L:
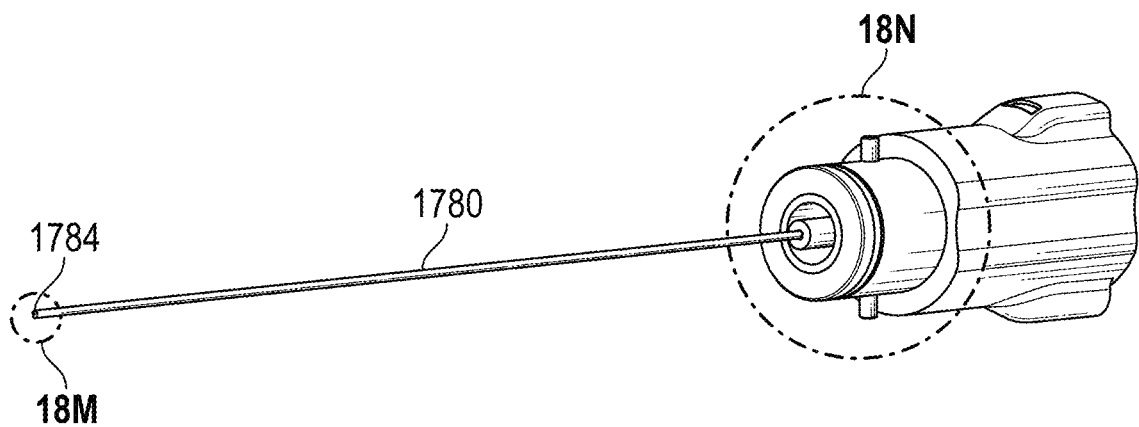
FIG. 18L is an isometric view of the handle of the device with the optical probe.
Figure 18M:
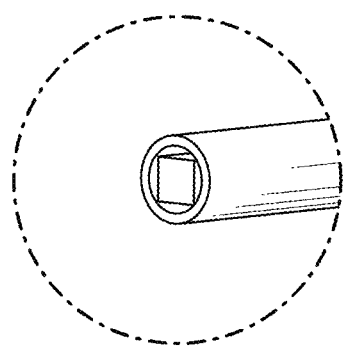
FIG. 18M shows a close up view of a distal end of the optical probe and FIG. 18N illustrates a close up view of a distal end portion of the handle.
Figure 18N:
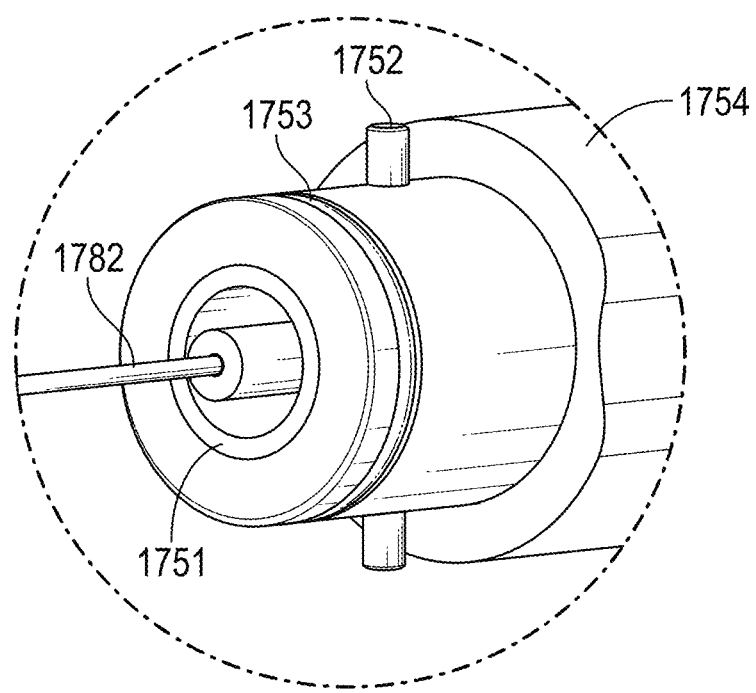

FIG. 18L is an isometric view of the handle of the device 1750 with the optical probe or stylet 1780, FIG. 18M shows a close up view of a distal end 1784 of the optical probe and FIG. 18N illustrates a close up view of a distal end portion of the handle 1750. As illustrated, the stylet 1780 can include a CMOS chip disposed in the lumen of a tubular member made, for example, from a stainless steel tube, such as a hypotube. A proximal end of the stylet 1780 is coupled to the handle portion 1750 of the device and accordingly to conductors that send image signals to a processor (not shown). A close up view of the distal portion of the handle portion 1750 in FIG. 18N illustrates a reduced diameter section that is received by a bore in the cannula 1710. This reduced diameter section includes a seal, such as an o-ring, 1753 to fluidly seal the cannula 1710 to the handle portion 1750 when they are connected. A pin 1752 on either side of the reduced diameter section is provided to engage the "J" connector. An insert 1751 can be seated in the housing of the handle 1750 that includes a female luer lock connector, for example.

If the exposed distal end of the stylet 1780 should become occluded in use by tissue fragments or the like, the stylet may be partially withdrawn into the lumen of the tube 1712 of the cannula 1710, and the flushing assembly 1760 may be activated to direct pressurized liquid, such as saline, down the bore of the cannula. Withdrawing the stylet into the cannula 1710 forces it to be immersed in a pressurized stream of liquid, which has been found to be an effective technique for cleaning the CMOS chip at the distal end 1784 of the stylet 1780. Once cleaned, the stylet can be reinserted into the bore to permit further visualization of the target site.

FIGS. 19A-19B illustrate full and partial isometric views of a spring loaded insufflation needle assembly in accordance with the present disclosure. This embodiment is similar to the embodiment 1700, but adds the feature of a spring loaded stylet 1980 and sheath 1920 residing in a sharpened cannula 1910 (FIG. 19B), wherein the sharpened tip of the cannula 1910 cuts tissue, and the sheath 1920 containing the optic is pushed back into the handle 1950 against a spring force that pushes the sheath and stylet 1980 forward after the sharpened distal tip of the cannula 1910 has traversed tissue and has entered the peritoneum. Sheath 1920 can have a connector 1922 at its proximal end that may function as a handle, and a distal end or tip 1924.

Figure 19C:
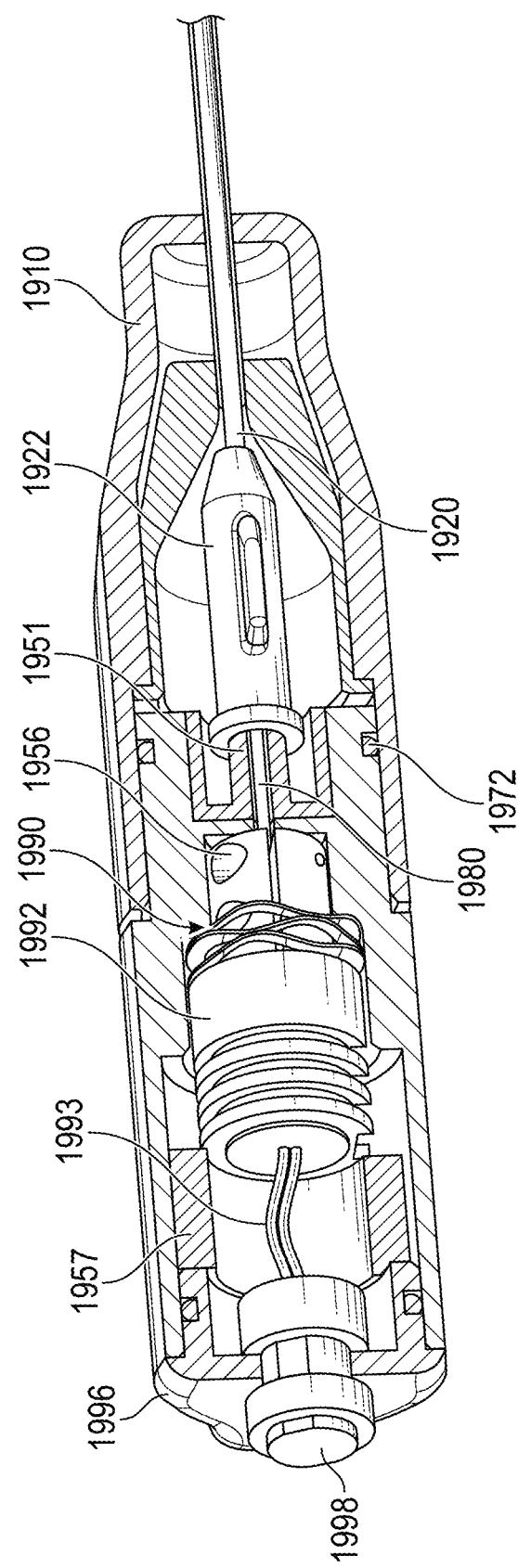
FIGS. 19C and 19D show cross sectional views of the device of FIG. 19A along a central axis of the device rotated 90 degrees with respect to each other.
Figure 19D:
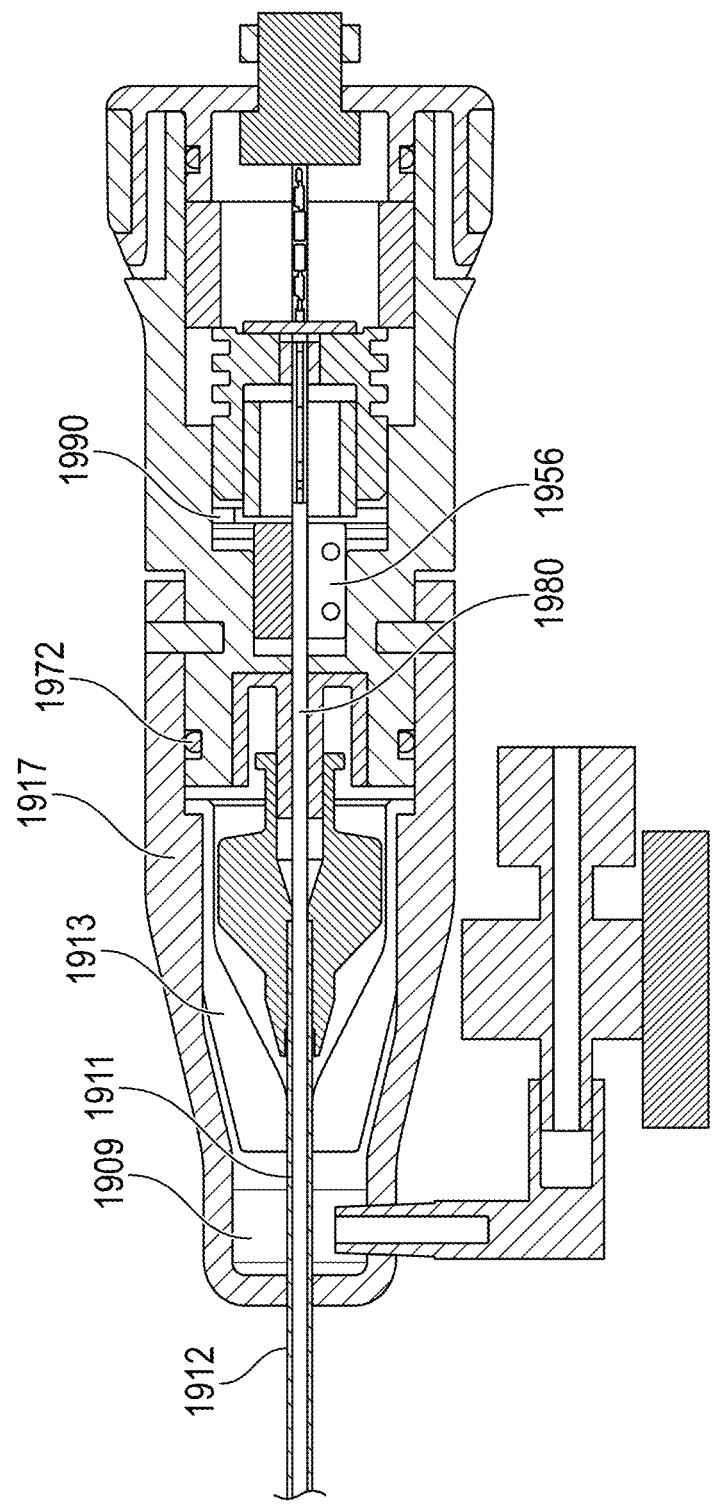

FIGS. 19C and 19D show cross sectional views of the device of FIG. 19A along a central axis of the device rotated 90 degrees with respect to each other. As can be seen, the cannula 1910 is connected to the housing by "J" connector. A luer connector insert 1951, as will be appreciated by those of skill in the art, is slidably received within a bore defined in a distal end of the housing and attached to stylet 1980. The luer connector permits the stylet 1980 to traverse through it, and the housing into a proximal cavity defined in the housing that in turn includes a stopper or connector 1956 that is attached to the stylet 1980. Proximal to the connector 1956 there resides a compression spring 1990 that pushes on the connector 1956, which pushes the stylet 1980, and consequently the sheath 1920 and insert 1951 distally with respect to the cannula shaft 1912 and out of the distal end of the cannula shaft to protect tissue once the cannula breaches the abdominal cavity (or other cavity). As is evident from FIG. 19C, for example, the stylet 1980 moves back and forth within the housing while attached to connector 1956 and insert 1951 to limit the proximal-distal movement of those components with respect to the housing 1950. A heat sink 1992 is disposed in the proximal cavity of the handle or housing 1950, wherein a distal end of the heat sink contacts the spring 1990, and a proximal end of the heat sink contacts a washer or spacer 1957. The annular spacer 1957 is bounded by the heat sink 1992 at its distal face, and at a cap 1996 at its proximal face. The proximal cavity of the handle is similarly sealed by an o ring disposed between the cap 1996 and the housing 1950. A connector 1998 is provided to connect to a power source and computer processor. Wires 1993 run from the connector to the LED housed in the heat sink 1992, wherein the LED shines light down fiber optic strands or other light transmissive material inside of the tube of the stylet 1980 that shines distally around the periphery of the CMOS chip. The cannula 1910, as can be seen, includes an inner body 1913, that is situated within the bore of the cannula. The inner body functions as a guide tube that is illustrated as being funnel shaped and defines a peripheral circumferential flange that seats against a peripheral circumferential shoulder defined in the cavity of outer body 1917. An o-ring 1972 or other seal can be provided within an annular groove formed into a distal reduced diameter section of housing 1950 to receive outer body 1917, wherein an outer surface body 1917 can function as a handle. The inner body 1913 and the outer body 1911 cooperate to define an axial bore therethrough to hold the proximal end or region of shaft 1912. Shaft can be attached to each of inner body 1913 and outer body 1917. Inner body 1913, outer body 1917 and shaft 1912 cooperate to define an annular cavity 1909 to receive flushing fluid by way of the flush port. The proximal end of shaft 1912 defines at least one fluid conduit 1911 therethrough to permit pressurized liquid from a syringe, for example, to be directed through the valve and the flushing system, into chamber 1909, through opening(s) 1911 and then down an annular lumen defined between the inner surface of the tubular shaft 1912 and the outer surface of the stylet 1980 or the outer surface of the sheath 1920, as appropriate.

FIGS. 19E-19H are views of an optical probe portion or stylet 1980 of the device of FIG. 19A. As can be seen, the stylet includes an elongate body that terminates in a distal end by way of the CMOS chip. Electrical conductors traverse up the tubular body of stylet 1980 to the heat sink 1992, where, from the cross section in FIG. 19H, it is apparent that an LED chip 1987 is mounted in a proximal bore of the heat sink 1992 that is coupled to electrical conductors that connect to an external connector 1998 that carries power to the LED, and carries out signal via the data cable. The LED element is centered on the axis of the device and directs light axially distally into the end of one or more fiber optic elements that traverse the bore of the stylet 1980 and terminate adjacent to the CMOS chip to provide direct illumination of a work area.

Figure 20A:
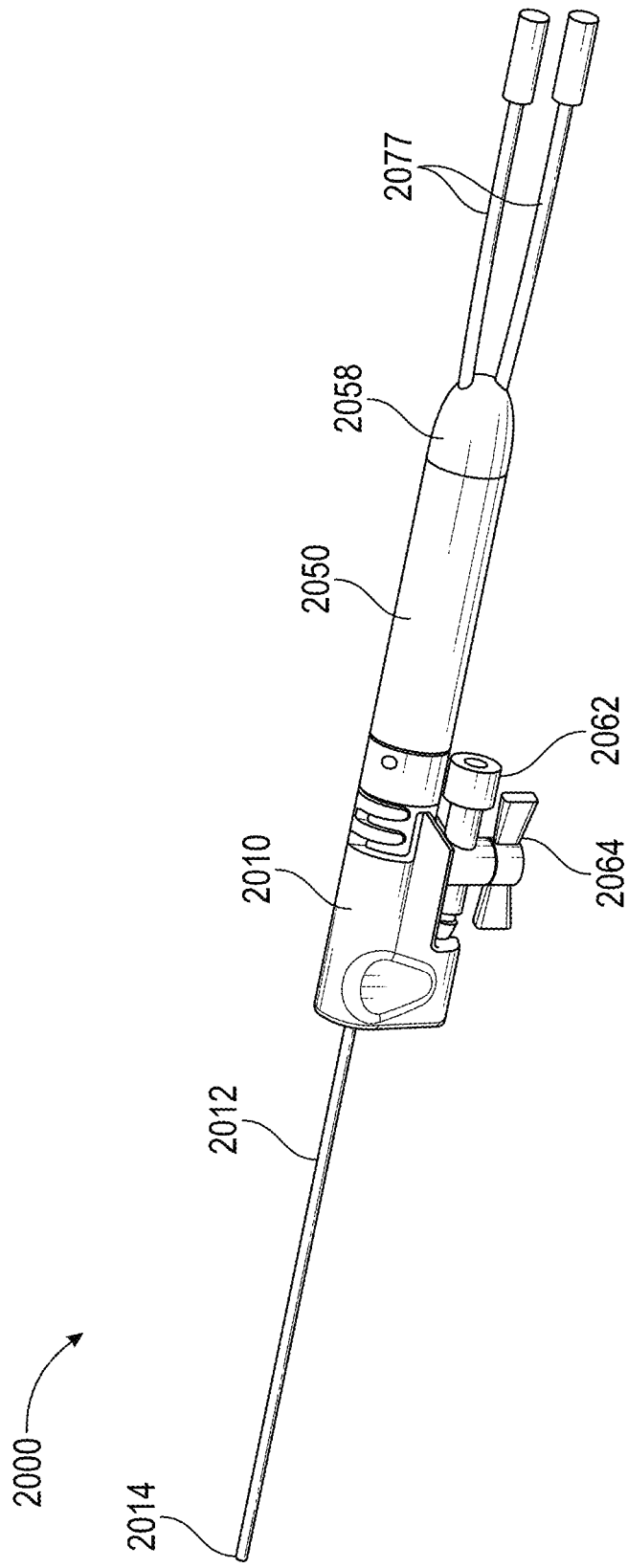
FIG. 20A is a view of a further embodiment of an insufflation needle assembly in accordance with the present disclosure.
Figure 20B:
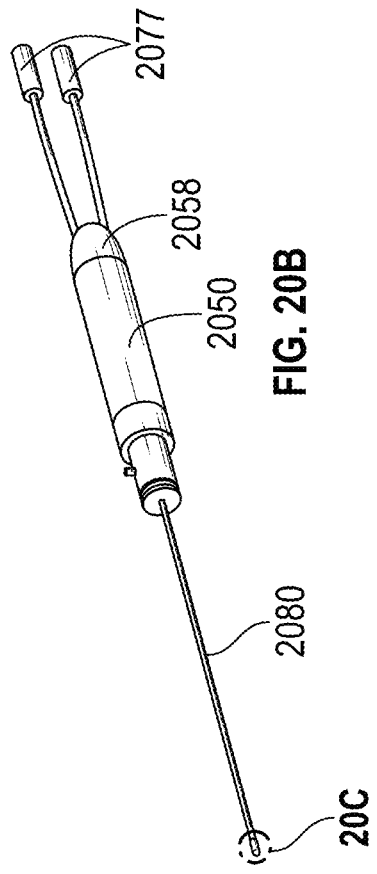
FIGS. 20B-20E show further aspects of the embodiment of FIG. 20A.
Figure 20C:
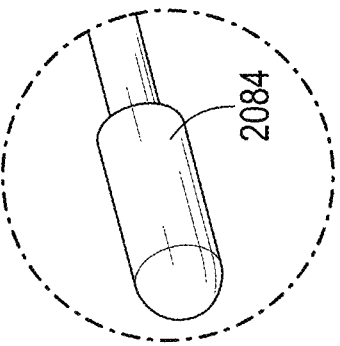
Figure 20D:
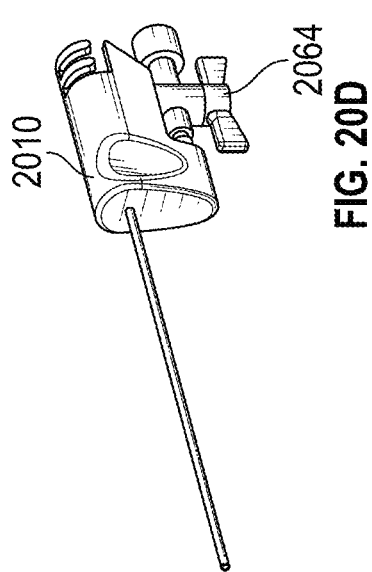
Figure 20E:
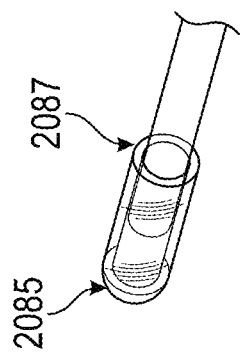

FIG. 20A is a view of a further embodiment of an insufflation needle assembly 2000 in accordance with the present disclosure. As depicted, the assembly includes a removable cannula 2010 that includes a distally extending tubular shaft 2012 through which a visualization stylet 2080 (FIG. 20B) traverses to a distal end 2014 thereof. A flush port 2062 is provided coupled to a valve 2064 can be used to flush the device 2000 and the distal tip of the stylet 2080 as with the embodiments 1700, 1900. Insufflation gas can be provided by way of port 2062 or other port, as desired. A proximal handle section 2050 is removably coupled to the cannula proximal portion, and includes a strain relief to provide a gradual change in stiffness to electrical conductors 2077.

FIGS. 20B-20E show further aspects of the embodiment of FIG. 20A with the cannula 2010 removed from the proximal portion of the device 2000. The cannula is removable from the proximal portion 2050 in the same manner as the previous embodiments using a "J" type coupling, but it will be appreciated that other types of connections can be used, such as an interference fit of various kinds, a keyed locking connection, and the like. The distal end 2084 of the stylet 2080 includes a rounded end 2085 and is attached, for example, but adhesive at location 2087 to the tube of the stylet 2080. The device 2000 can be configured as a small visualization trocar as with embodiment 1700, wherein the distal end of the cannula 2010 is not sharpened and the tip 2085 includes a dissecting tip that can be cleaned after insertion by withdrawing it proximally into cannula and clean fluid is flushed over it via valve 2064.

Figure 20F:
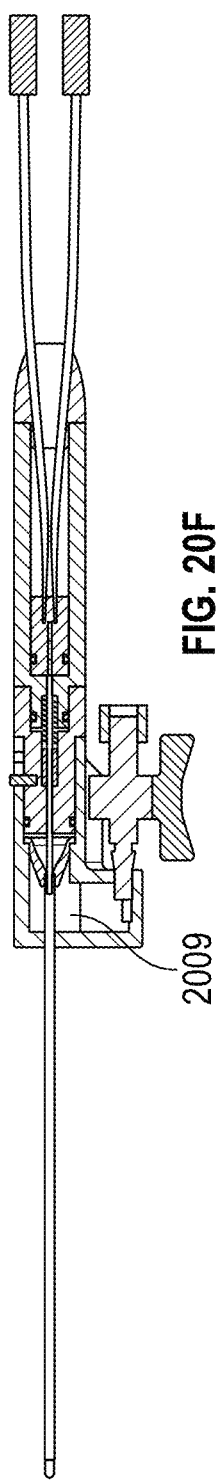
Figure 20G:
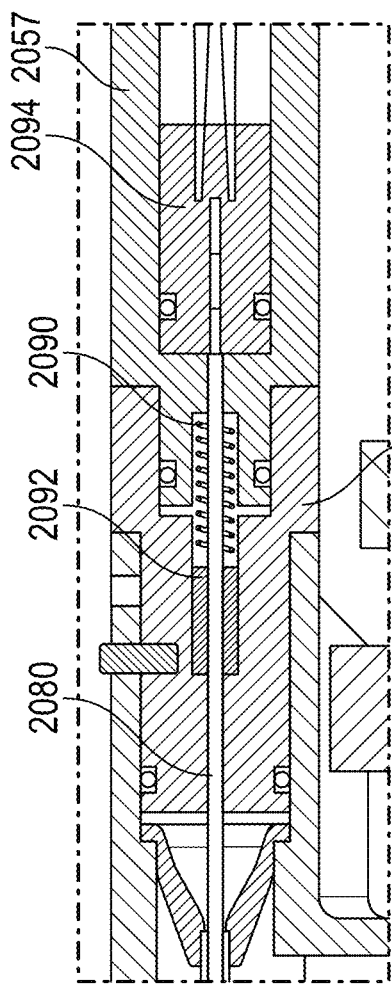
Figure 20H:
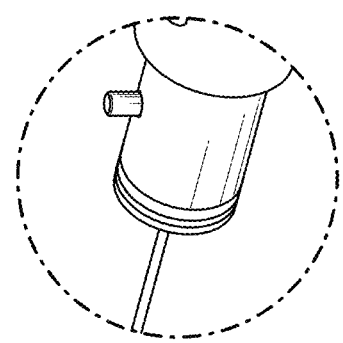
Figure 20I:
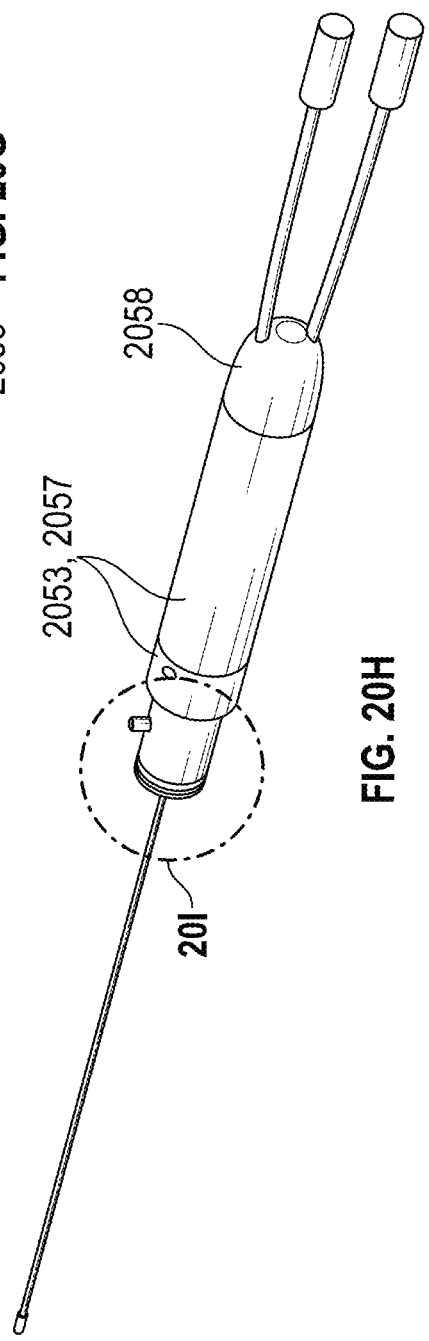

FIGS. 20E-20I show still further aspects of the embodiment of FIG. 20A. FIG. 20F presents a central cross section down the central axis of the device 2000, FIG. 20G presents an enlarged section of that cross section, FIG. 20I presents a close up view of the distal end portion of the housing of the device, and FIG. 20H presents a rear isometric view of device 2000 with the cannula 2010 removed. A compression spring 2090 surrounds the stylet 2080, and is housed in a central axial bore that ids defined in both distal handle segment 2053 and proximal handle segment 2057. A boss 2092, illustrated in the form of a tube surrounding the stylet 2080, is adhered to the stylet 2080, and the compression spring 2090 urges the boss distally by pushing it away from the proximal housing segment 2057. This results in the stylet and its rounded distal end protruding from the sharpened distal end of the cannula 2010. The stylet 2080 is coupled at its proximal end to a bushing 2094 that can include an LED element disposed therein that slides within a corresponding central axial bore defined along a proximal portion of proximal housing segment 2057. Seals, such as o-ring seals, surround the distal housing segment 2053 to form a fluid tight seal with an inner cylindrical bore formed in the proximal end portion of the cannula 2010. Conductors that traverse the length of the stylet 2080 extend through a proximal end of the bushing 2094 and extend proximally through the strain relief 2058 for coupling to a processor and/or electrical power source.

Figure 20J:
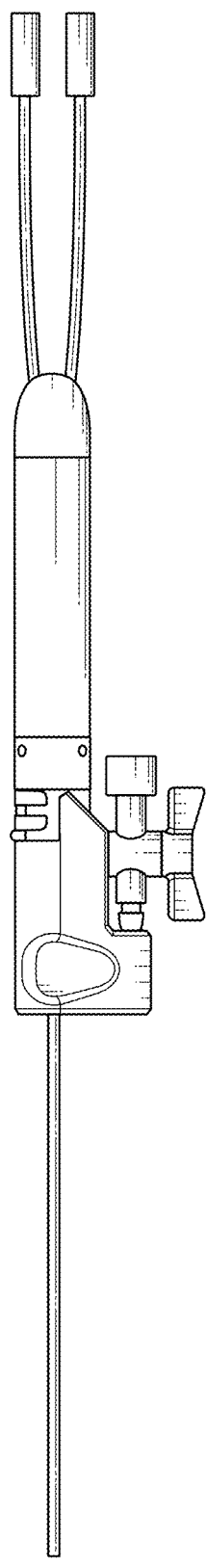
FIGS. 20J-20L depict schematic views of the embodiment of FIG. 20A.
Figure 20K:
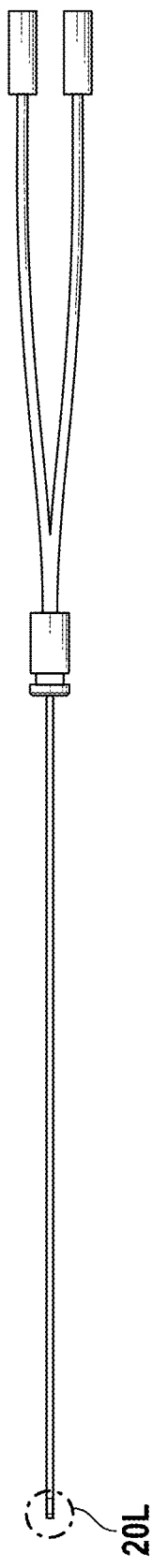
Figure 20L:
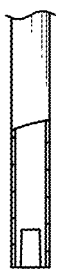

FIGS. 20J-20L depict schematic views of aspects of the embodiment of FIG. 20A. FIG. 20J illustrates a schematic side view of the cannula assembly 2000 and FIG. 20K illustrates a side view of the visualization stylet from its proximal connectors to its distal end and associated bushing that attaches to the proximal end of the stylet shaft and the distal ends of the conductor lines.

Thus, embodiments are disclosed that can be used as a miniature visualization trocar, or as a Veress-style needle with visualization. Nominally, the optical trocar or needle can have a 2.2 mm outer diameter, for example, a removable outer cannula, and a refastenable connector, such as a "J" type connector. The devices can include snap or interference fits, and a removable visualization stylet to accomplish the techniques set forth herein. Embodiments 1700, 1900, 2000 can utilize a "J" connector or other connector having two axial positions of the cannula with respect to the inner stylet or sheath as illustrated to permit the stylet to be withdrawn slightly to perform a flushing and cleaning operation by injecting fluid through the fluid port and down the shaft of the cannula and around the distal tip of the visualization stylet or sheath. The insufflation needles can be provided with an audible and/or tactile indication of entry by making a "clicking" noise after the peritoneum has been breached so the surgeon knows to stop pushing the device.

In accordance with another embodiment, the Veress needle is inserted as set forth above under direct visualization. The outer cannula is removed by first disconnecting the inner stylet from an electrical connector so the outer cannula can slide up over it. This leaves the inner cannula in place. Then, a second, larger cannula (e.g., having a 5 mm or 10 mm diameter passage, and optionally having an insufflation port) is slid over the inner visualization stylet to dilate the tissue radially outwardly. The visualization stylet can be left in place, or it too can be removed so that a further instrument can be introduced through the newly placed cannula. For example, a larger scope with a larger light source and photodetector array can be inserted to provide improved imaging. Advantageously, this permits entry into the peritoneum under direct visualization using a small instrument, and permits insertion of a much larger trocar without need for an obturator. This can be very important, as there are many documented instances where surgeons have attempted to insert an obturator with a larger trocar in the first instance, resulting in damaging internal structures such as bowels, or in severe cases, the abdominal aorta, resulting in death of the patient. As will be appreciated, trocars that are used and slid over the inner stylet preferably include outer ribs to prevent undesirable axial trocar movement during the procedure.

While it is contemplated that the devices disclosed herein are generally configured to access the peritoneum, it will be appreciated that the disclosed embodiments can be used to access any desired portion of the anatomy, such as the abdominal cavity, the pelvic cavity, the thoracic cavity, sinus passages, and the like, as well as be connected to a robotic manipulator to permit the disclosed embodiments to be utilized in robotic surgery. In further accordance with the disclosure, PCT/US2019/065723, filed Dec. 11, 2019 (which is incorporated by reference herein in its entirety) discusses a procedure including introducing a needle through the vagina and into the cul de sac to define a passageway through which a visualization scope can pass. This can support a diagnostic procedure, such as subsequently aspirating fluid or obtaining a tissue sample, for example. A therapeutic procedure can be performed such as delivering a beneficial agent to tissue in the cul de sac, among other things. The present disclosure further includes using any suitable device as set forth herein, such as device 1700, to be used in this procedure to enter through the posterior cul de sac via the vagina under direct vision. The visualization stylet (e.g., 1720, 1780) can then be withdrawn, and the visualization scope of PCT/US2019/065723 can then be inserted into the cul de sac via cannula 1710 and inspect the pelvic cavity in that manner. This can be done in conjunction with hysteroscopy, wherein the uterine cavity is filled with saline. Given the pressure of the hysteroscope, there will be some fluid that flushes through the fallopian tubes and into the peritoneal cavity. This fluid can then be aspirated by the scope device in PCT/US2019/065723 and the aspirated sample can then be sent to pathology.

In accordance with further embodiments, the outer sleeves of the insufflation needle disclosed herein can be blunted or dulled, and instead a relatively sharper tip can be provided on the inner visualization stylet. In this instance, a minimal spring mechanism, or no spring mechanism can be used, and the tip of the visualization stylet, while sharper, need not be extremely sharp because of its small diameter. These aspects can be applied to any embodiment of this disclosure.

It will be appreciated that one or more of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the present disclosure.

What is claimed is:

1. A surgical instrument, comprising:
a distal outer assembly including a distal housing having
a hollow distally extending needle extending distally therefrom, the hollow distally extending needle having a distal end and a proximal end, wherein the distal outer assembly forms a passageway to pass at least one of fluid and instruments therethrough;

a visualization stylet assembly at least partially disposed within the passageway of the distal outer assembly, the visualization stylet assembly being removably coupled to the distal outer assembly, the visualization stylet assembly including:

an elongate body having a proximal end and a distal end;

an electronic photodetector chip mounted proximate the distal end of the elongate body, the electronic photodetector chip having a distally facing surface to detect incoming light traveling along a proximal direction;

a light source at least partially integrated into the elongate body to project light beyond the electronic photodetector chip in a distal direction to provide direct illumination; and a sleeve slidably disposed about at least a distal tip region of the removable visualization stylet assembly, the sleeve including a lens element disposed at a distal end thereof to direct light through the lens element toward the electronic photodetector chip, wherein at least a portion of the sleeve extends proximally through the hollow distally extending needle and terminates in a location proximal to the proximal end of the hollow distally extending needle, and further wherein the distal outer assembly and the removable visualization stylet assembly can be decoupled to permit removal of the sleeve after the hollow distally extending needle has been introduced into a patient.

2. The surgical instrument of claim 1, wherein the visualization stylet assembly further includes a connector body disposed concentrically about a proximal region of the elongate body, the connector body including a distally facing connector to removably couple to a handle portion of the sleeve.

3. The surgical instrument of claim 1, wherein the visualization stylet assembly further includes a connector body disposed concentrically about a proximal region of the elongate body, the connector body including a distally facing connector to removably couple to a handle portion of the sleeve, the connector body being received at least partially within the proximal housing of the surgical instrument.

4. The surgical instrument of claim 3, wherein the handle portion of the sleeve includes a female locking member that is received by a male locking member of the connector body to permit the sleeve to be selectively decoupled from the visualization stylet assembly to expose the electronic photodetector chip.

5. The surgical instrument of claim 4, wherein the proximal housing defines a distally extending boss to be sealingly received by the distal outer assembly, and further wherein the distally extending boss is surrounded by a fluid tight seal to interface with an inwardly facing surface of the distal outer assembly.

6. The surgical instrument of claim 5, wherein the distal outer assembly further includes a guide tube disposed within the passageway of the distal outer body to guide the visualization stylet assembly into the hollow distally extending needle.

7. The surgical instrument of claim 6, wherein the visualization stylet assembly further includes a heat sink at least partially disposed within the proximal housing to dissipate heat generated by the surgical instrument.

8. The surgical instrument of claim 7, wherein the proximal housing defines a proximal cavity in which the elongate body of the visualization stylet assembly terminates at the proximal end of the elongate body, and further wherein at least one cable extends from the proximal end of the elongate body through the proximal cavity, through the heat sink, and to a connector located within a proximal cap of the proximal housing.

9. The surgical instrument of claim 7, wherein the heat sink includes a proximal end, a distal end and defines a bore at least partially therethrough, and further wherein a LED chip is mounted at least partially within the bore of the heat sink, the LED chip including a distally facing LED to direct light into the visualization stylet to provide forward illumination.

10. The surgical instrument of claim 1, wherein the distal housing includes a flush port operably coupled thereto, the flush port being configured to direct a liquid from a source of liquid through the flush port, into the housing and through the hollow distally extending needle.

11. A method comprising providing a device according to claim 10, operably coupling the flush port to the source of liquid, and directing liquid from the liquid source through the hollow distally extending needle into an anatomical region of a patient.

12. The surgical instrument of claim 1, wherein the lens element includes at least one edge for dissecting tissue.

13. The device of claim 12, wherein the at least one edge includes at least one fin.

14. The device of claim 12, wherein the at least one edge includes a plurality of fins.

15. A method comprising providing a device according to claim 1, introducing the hollow distally extending needle into an anatomical region of a patient, and inspecting at least one anatomical feature inside the patient using the visualization stylet.

16. The method of claim 15, further comprising withdrawing the visualization stylet assembly and from the hollow distally extending needle, removing the sleeve from the visualization stylet assembly, and introducing the visualization stylet assembly through the hollow distally extending needle into the anatomical region of the patient.

17. The method of claim 15, further comprising insufflating the peritoneum, wherein the at least one anatomical feature resides within the peritoneum.

18. The surgical instrument of claim 1, wherein the lens element includes an atraumatic distal tip.

19. The surgical instrument of claim 1, further comprising at least one cable extending proximally from a proximal end of the visualization stylet assembly.

20. The surgical instrument of claim 19, further comprising a strain relief operably coupled to the proximal end of the visualization stylet assembly to provide a transition in stiffness for the at least one cable.

* * * * *